United States Patent
Le et al.

(10) Patent No.: US 10,028,703 B2
(45) Date of Patent: Jul. 24, 2018

(54) WEARABLE SYSTEM FOR DETECTING AND MEASURING BIOSIGNALS

(71) Applicant: Emotiv Lifesciences Inc., San Francisco, CA (US)

(72) Inventors: Tan Le, San Francisco, CA (US); Geoffrey Mackellar, San Francisco, CA (US)

(73) Assignee: Emotiv, Inc., San Francisco, CA (US)

( * ) Notice: Subject to any disclaimer, the term of this patent is extended or adjusted under 35 U.S.C. 154(b) by 1029 days.

(21) Appl. No.: 14/447,298

(22) Filed: Jul. 30, 2014

(65) Prior Publication Data

US 2016/0029958 A1 Feb. 4, 2016
US 2017/0303854 A9 Oct. 26, 2017

Related U.S. Application Data

(60) Provisional application No. 61/859,887, filed on Jul. 30, 2013, provisional application No. 61/859,886, filed on Jul. 30, 2013.

(51) Int. Cl.

| | |
|---|---|
| *A61B 5/04* | (2006.01) |
| *A61B 5/00* | (2006.01) |
| *A61B 5/0492* | (2006.01) |
| *A61B 5/0478* | (2006.01) |

(Continued)

(52) U.S. Cl.
CPC ........ *A61B 5/6835* (2013.01); *A61B 5/02055* (2013.01); *A61B 5/04008* (2013.01); *A61B 5/0478* (2013.01); *A61B 5/04085* (2013.01); *A61B 5/0492* (2013.01); *A61B 5/0496* (2013.01); *A61B 5/1112* (2013.01);

(Continued)

(58) Field of Classification Search
CPC ... A61B 5/0478; A61B 5/0476; A61B 5/6803; A61B 5/0024; A61B 5/4094; A61B 5/6814; A61B 5/04012; A61B 5/04001; A61B 5/0484; A61B 5/0006; A61B 5/4064; A61B 5/04085; A61B 5/165; A61B 5/4076; A61B 5/725; A61B 5/4806;

(Continued)

(56) References Cited

U.S. PATENT DOCUMENTS

| | | | |
|---|---|---|---|
| 6,201,982 B1 * | 3/2001 | Menkes | A61B 5/0478 600/383 |
| 6,510,333 B1 * | 1/2003 | Licata | A61B 5/04026 600/383 |

(Continued)

FOREIGN PATENT DOCUMENTS

WO 087486 7/2009

*Primary Examiner* — Joseph Stoklosa
*Assistant Examiner* — Brian M Antiskay
(74) *Attorney, Agent, or Firm* — Jeffrey Schox; Diana Lin

(57) ABSTRACT

A system for detecting bioelectrical signals of a user comprising: a set of sensors configured to detect bioelectrical signals from the user, each sensor in the set of sensors configured to provide non-polarizable contact at the body of the user; an electronics subsystem comprising a power module configured to distribute power to the system and a signal processing module configured to receive signals from the set of sensors; a set of sensor interfaces coupling the set of sensors to the electronics subsystem and configured to facilitate noise isolation within the system; and a housing coupled to the electronics subsystem, wherein the housing facilitates coupling of the system to a head region of the user.

20 Claims, 11 Drawing Sheets

(51) Int. Cl.
*A61B 5/0408* (2006.01)
*A61B 5/0205* (2006.01)
*A61B 5/11* (2006.01)
*A61B 5/0496* (2006.01)
*A61B 5/024* (2006.01)
*A61B 5/0245* (2006.01)
*A61B 5/053* (2006.01)
*A61B 5/0488* (2006.01)

(52) U.S. Cl.
CPC .......... *A61B 5/6803* (2013.01); *A61B 5/6814* (2013.01); *A61B 5/7217* (2013.01); *A61B 5/0245* (2013.01); *A61B 5/02405* (2013.01); *A61B 5/04012* (2013.01); *A61B 5/0488* (2013.01); *A61B 5/0533* (2013.01); *A61B 5/1126* (2013.01)

(58) Field of Classification Search
CPC ................ A61B 5/4812; A61B 5/6831; A61B 2018/00446; A61N 1/0484; A61N 1/0531
USPC ............... 600/372, 382, 384, 386, 388–393, 600/544–545; 607/115–118
See application file for complete search history.

(56) References Cited

U.S. PATENT DOCUMENTS

| | | | |
|---|---|---|---|
| 7,714,757 B2 | 5/2010 | Denison et al. | |
| 8,150,624 B2 | 4/2012 | Berardi et al. | |
| 8,242,429 B2 | 8/2012 | Sarpeshkar et al. | |
| 8,332,024 B2 | 12/2012 | Rapoport et al. | |
| 8,655,428 B2* | 2/2014 | Pradeep | A61B 5/0476 600/383 |
| 8,989,836 B2* | 3/2015 | Machon | A61B 5/6803 600/383 |
| 9,615,793 B2 | 4/2017 | Solosko et al. | |
| 2002/0029005 A1* | 3/2002 | Levendowski | A61B 5/0478 600/545 |
| 2004/0012410 A1* | 1/2004 | Liu | H03K 19/018528 326/81 |
| 2006/0258930 A1* | 11/2006 | Wu | A61B 5/0002 600/383 |
| 2007/0060831 A1 | 3/2007 | Le et al. | |
| 2007/0093706 A1* | 4/2007 | Gevins | A61B 5/0478 600/383 |
| 2007/0191727 A1* | 8/2007 | Fadem | A61B 5/0002 600/544 |
| 2007/0225585 A1 | 9/2007 | Washbon et al. | |
| 2008/0027345 A1* | 1/2008 | Kumada | A61B 5/0478 600/383 |
| 2009/0105576 A1 | 4/2009 | Do et al. | |
| 2009/0112077 A1* | 4/2009 | Nguyen | A61B 5/0478 600/383 |
| 2009/0163781 A1 | 6/2009 | Say et al. | |
| 2011/0257502 A1 | 10/2011 | Lee | |
| 2013/0012802 A1* | 1/2013 | Horseman | A61B 5/0476 600/383 |
| 2015/0313496 A1* | 11/2015 | Connor | A61B 5/0476 600/301 |
| 2017/0027466 A1* | 2/2017 | Kerth | A61B 5/0478 |

* cited by examiner

WEARABLE SYSTEM FOR DETECTING AND MEASURING BIOSIGNALS

CROSS-REFERENCE TO RELATED APPLICATIONS

This application claims the benefit of U.S. Provisional Application Ser. No. 61/859,887 filed 30 Jul. 2013 and U.S. Provisional Application Ser. No. 61/859,886 filed 30 Jul. 2013, which are both incorporated in their entirety herein by this reference.

TECHNICAL FIELD

This invention relates generally to the biosignals field, and more specifically to a new and useful system for detecting and measuring biosignals.

BACKGROUND

The general populace interacts with a wide variety of sensors on a daily basis, and vast amounts of data pertaining to individuals and entire groups of people is collected from these sensors. This data can be anchored in the physical realm, such as location data provided through a GPS sensor, caloric expenditure provided by an exercise machine, footstep count provided by an accelerometer-based step counter, or heart rate, body temperature, respiratory rate, or glucose level provided by a biometric sensor. This data can also be more abstract, such as interests as indicated by websites visited or needs as indicated by purchases made through an online store. This data can provide significant insight into market trends, needs, and interests of a particular demographic, and this data can even be used to target a user with particular physical and digital goods and services. However, contemporary sensors, data collection, and data analysis fail to capture cognitive, mental, and affective states of individuals and groups of people that can provide similar insight. Furthermore, contemporary data collection fails to efficiently locate, obtain, and aggregate biosignal data from multiple or selected individuals and make this data available for analysis. Thus, there is a need in the biosignals field for a new and useful system for detecting and measuring biosignals.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. System

Figure 1A:
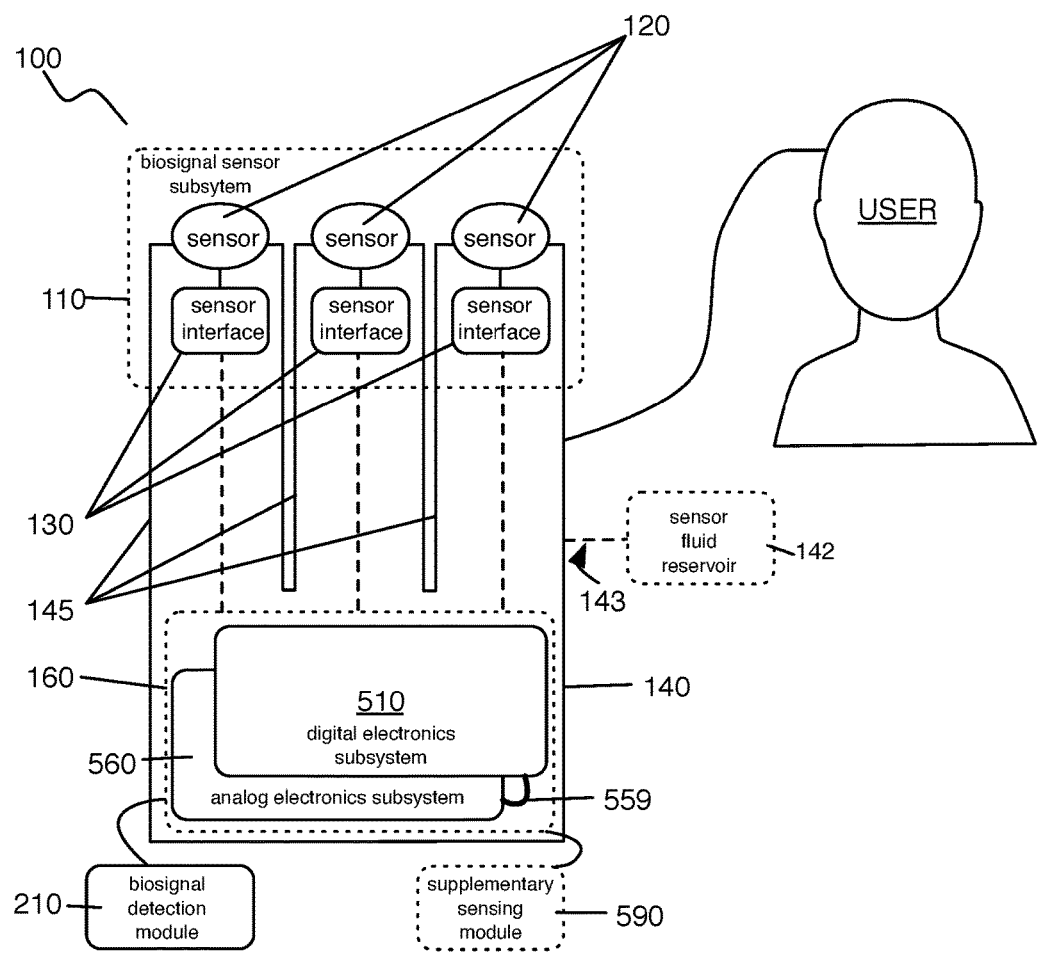
FIGS. 1A and 1B depict an embodiment of a system for detecting and measuring biosignals.
Figure 1B:
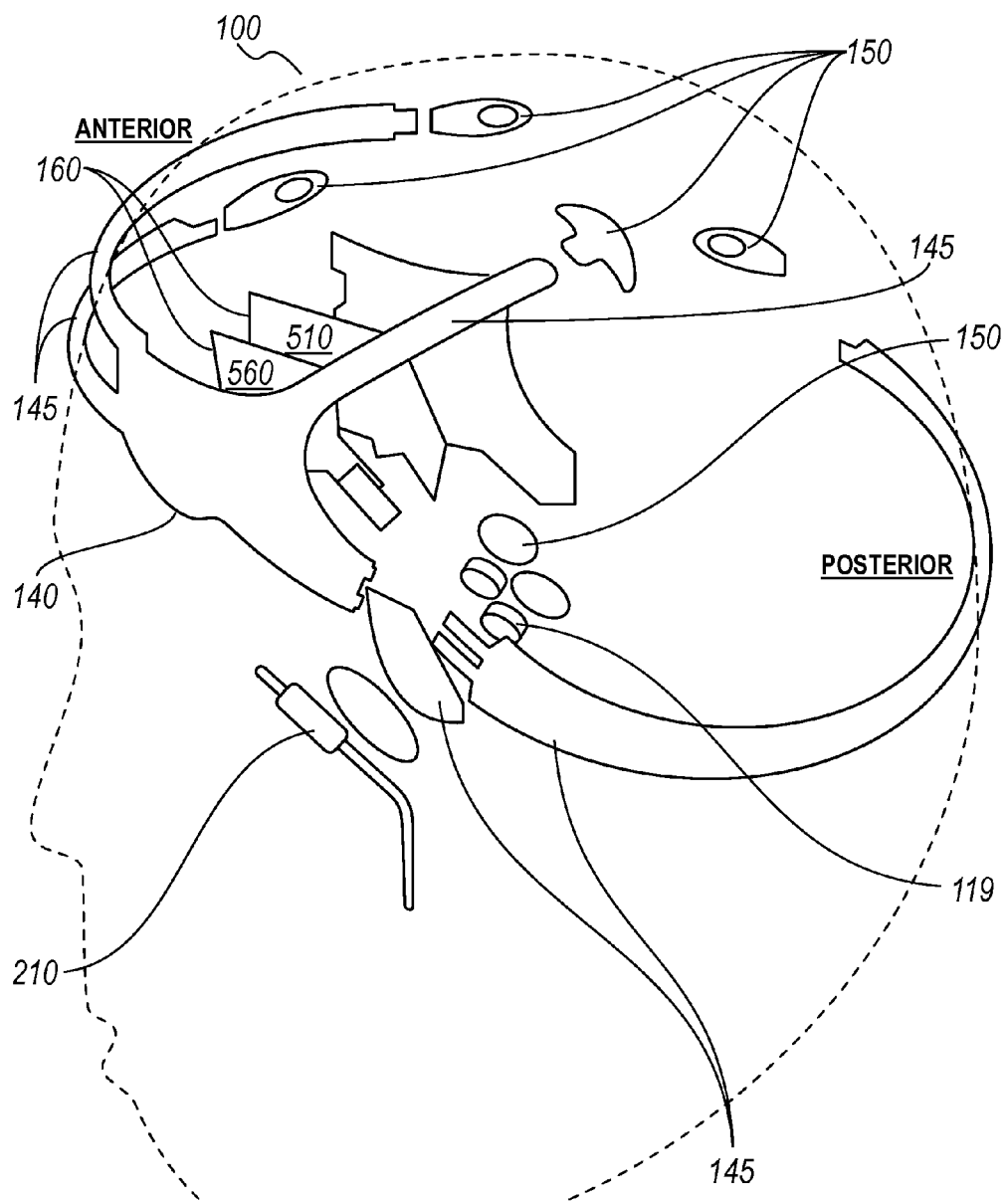

As shown in FIGS. 1A and 1B, an embodiment of a system 100 for detecting and measuring biosignals of a user comprises: a biosignal sensor subsystem 110 comprising a set of sensors 120 configured to detect biosignals from the user and a set of sensor interfaces 130 configured to pre-process signals from the set of sensors 120; a housing 140 including a set of arms 145 configured to couple to the set of sensors 120 by a set of sensor couplings 150, such that the system 100 can be worn by the user; and an electronics subsystem 160 coupled to the biosignal sensor subsystem 110 and configured to power the system 100 and facilitate processing of biosignals detected by the system 100. The system 100 functions to provide a biosignal sensing tool for a user, a group of users, or an entity associated with the user/group of users, in a format that is wearable. Thus, the system 100 is preferably configured to be worn by a user as the user performs activities (e.g., watching videos, receiving stimuli, exercising, reading, playing sports) in his/her daily life.

Preferably, the biosignals detected and measured by the system 100 comprise bioelectrical signals; however, the biosignals can additionally or alternatively comprise any other suitable biosignal data. In variations of the system 100 for bioelectrical signal detection and measurement, the system 100 is preferably configured to detect electroencephalograph (EEG) signals, which can be reflective of cognitive, mental, and affective state of the user. However, the bioelectrical signals can additionally or alternatively include any one or more of: signals related to magnetoencephalography (MEG) impedance or galvanic skin response (GSR), electrocardiography (ECG), heart rate variability (HRV), electrooculography (EOG), and electromyelography (EMG). Other variations of the system 100 can additionally or alternatively comprise sensors configured to detect and measure other biosignals, including biosignals related to cerebral blood flow (CBF), optical signals (e.g., eye movement, body movement), mechanical signals (e.g., mechanomyographs) chemical signals (e.g., blood oxygenation), acoustic signals, temperature, respiratory rate, positional information (e.g., from a global positioning sensor), motion information (e.g., from an accelerometer and/or a gyroscope with any suitable number of axes of motion detection), and/or any other signals obtained from or related to biological tissue or biological processes of the user, as well as the environment of the user. Positional information can, for example, provide information to an emergency response team in the event that an adverse mental condition (e.g., a seizure) is detected at the system 100. Furthermore, motion information can enable determination of user gait, activity, tremors, and other details pertinent to the diagnosis or characterization of the user's situation, and can additionally or alternatively facilitate correction of and/or compensation for motion artifacts in biosignals detected at the system 100.

The system 100 is preferably configured to be wearable by a user, require little maintenance, and maintain contact between the set of sensors and the user as the user performs activities in his/her daily life. As such, the system 100 is preferably comfortable for long term use, aesthetically pleasing, includes sufficient power storage, and adapts in response to the user's motions, in order to maintain contact with the user. The system 100, however, can be configured in any other suitable manner that enables detection and/or measurement of biosignals of the user.

1.1 System—Biosignal Sensor Subsystem

As shown in FIGS. 1A and 1B, the biosignal sensor subsystem 110 comprises a set of sensors 120 and is configured to interface with an electronics subsystem 160 by a set of sensor interfaces 130. The biosignal sensor subsystem 110 preferably functions to detect EEG signals from the brain of a user, but can additionally or alternatively be configured to detect any other biosignal or environmental signal of the user.

The set of sensors 120 functions to directly detect biosignals (e.g., bioelectrical signals) from a user, wherein each sensor in the set of sensors 120 is configured to provide at least one channel for signal detection. Preferably, each sensor in the set of sensors 120 is identical to all other sensors in composition; however, each sensor in the set of sensors 120 can be non identical to all other sensors in composition, in order to facilitate unique signal detection requirements at different region of the user's body (e.g., user's brain). The set of sensors 120 can comprise sensors that are non-identical in morphology, in order to facilitate application at different body regions; however, the set of sensors 120 can alternatively comprise sensors that are identical in morphology. The set of sensors 120 can be placed at specific locations on the user, in order to detect biosignals from multiple regions of the user. Furthermore, the sensor locations can be adjustable, such that the set of sensors 195 can be tailored to each user's unique anatomy. Alternatively, the biosignal sensor system 110 can comprise a single sensor configured to capture signals from a single location, and/or can comprise sensors that are not adjustable in location.

Preferably, each sensor in the set of sensors 120 provides a single channel for signal detection, such that the number of sensors correspond to the number of channels for signal detection in a one-to-one manner; however, the set of sensors 120 can alternatively provide any other suitable number of channels for signal detection relative to a number of sensors in the set of sensors 120. For instance, in one variation, multiple sensors of the set of sensors 120 can be configured to provide one channel for signal detection, such that the number of channels for signal detection is smaller than the number of sensors in the set of sensors 120. Preferably, the set of sensors 120 can provide electrical characteristics (e.g., frequency bandwidth, nominal voltage range, etc.) to accommodate electroencephalographic signals and electromyographic signals; however, the set of sensors 120 can alternatively be configured to accommodate only electroencephalographic signals or to accommodate any other suitable type(s) of signals. In a specific example, each sensor in the set of sensors 120 is characterized by a frequency bandwidth from 0 to 80 Hz, and is characterized by a nominal voltage of 10-100 microvolts. In a variation of the specific example, each sensor in the set of sensors 120 can accommodate large electromyographic signals (e.g., eye blinks, clenched jaw signals) characterized by nominal voltages in the millivolt range (e.g., 5 millivolts).

The set of sensors 120 can comprise sensors configured to detect signals through the user's skin and/or hair, and preferably comprises electrically conductive sensor pads that provide low to moderate contact impedances and low-voltage signal transmission. The sensors of the set of sensors 120 are also preferably low-noise, and/or provide non-polarizable contact with the user's skin. As such, the sensors preferably behave such that the contact half-cell voltage (i.e., voltage potential across electrode and electrolyte separated by a Helmholtz layer) is independent of current magnitude or direction of flow in relation to a sensor in a particular range of interest. However, the sensors can alternatively comprise sensors with any other suitable noise-handling and/or polarizability behavior. The sensors are preferably comfortable to wear for long periods of usage, conform to the user's skin (e.g., by morphological configuration, by morphological transformation, by morphological deformation upon application to the user), are characterized by a surface with a sufficiently high coefficient of friction, such that the sensors do not readily slip or move relative to the user after application to the user, are non-toxic, and/or are hypoallergenic. However, the sensor pads of the set of sensors 120 can be characterized by any other suitable user comfort characteristic(s), morphological behavior, and/or friction characteristic(s).

The sensors preferably include sensor pads 119 characterized as "dry sensors" or "semi-dry sensors" that either comprise no fluid, or comprise a non-volatile fluid (e.g., are saturated with a non-volatile fluid), such that the dry sensors require little maintenance with regard to maintaining a "wet" state. In variations comprising dry/semi-dry sensors, non-polarizable contact is preferable to reduce or eliminate variability in signal detection and/or reception. Signal detection and/or reception are dependent upon an impedance of an interface of contact between the sensor and the user (e.g., the impedance of a sensor-user interface), which can vary over several orders of magnitude with dry/semi-dry sensors. The dry sensor pad 119 material preferably facilitates generation of a continuous (e.g., unbroken) interface between the sensor and the user. As such, the dry sensor pad material preferably evolves a volume of fluid (e.g., a thin film of fluid at a sensor-user interface), and can additionally or alternatively stimulates perspiration by the user at the sensor-user interface and/or attracts environmental moisture, in order to provide a continuous sensor-user interface. In variations wherein the dry sensor pad 119 material evolves a volume of fluid, the fluid is preferably non-volatile, and the dry sensor pad 119 material preferably is configured to absorb environmental moisture to extend its usable life before maintenance is required. Furthermore, the dry sensor pad 119 material is configured to redistribute fluid (e.g., to depleted regions, to depleted surface layers) passively by internal diffusion; however, the dry sensor pad material can be coupled to a fluid distribution module configured to actively redistribute and/or resupply fluid to depleted sensor regions. In one example, the dry sensor pad 119 comprises a hydrogel polymer (e.g., silicone hydrogel, polyhydroxyethylmethacrylate hydrogel, polymethylmethacrylate hydrogel) saturated with a nonvolatile, electrically conducting electrolyte fluid. In the example, the electrolyte fluid is configured to exude the electrolyte fluid upon application of the sensor to the user and/or upon subjecting the sensor pad 119 material to pressure, in order to provide a continuous sensor-user interface. In other variations, the sensor pads can alternatively comprise "wet sensors" composed of a hydrated material (e.g., hydrogel, porous material) that loses moisture at a rate higher than that of the dry sensors. In variations with wet sensors, the wet sensor material can be configured to absorb fluid prior to sensor placement, after sensor placement, and/or at any other suitable time relative to placement of the sensor(s) on the user's body. In still other variations, the sensor pads can comprise hybrid sensors composed of a composite wet/dry sensor material, or any other suitable sensor material configured to provide sufficient signal detection and transmission. Preferably, the materials used in the set of sensors are 120 are hypoallergenic; however, the set of sensors can additionally or alternatively utilize any other suitable material(s).

Figure 1C:
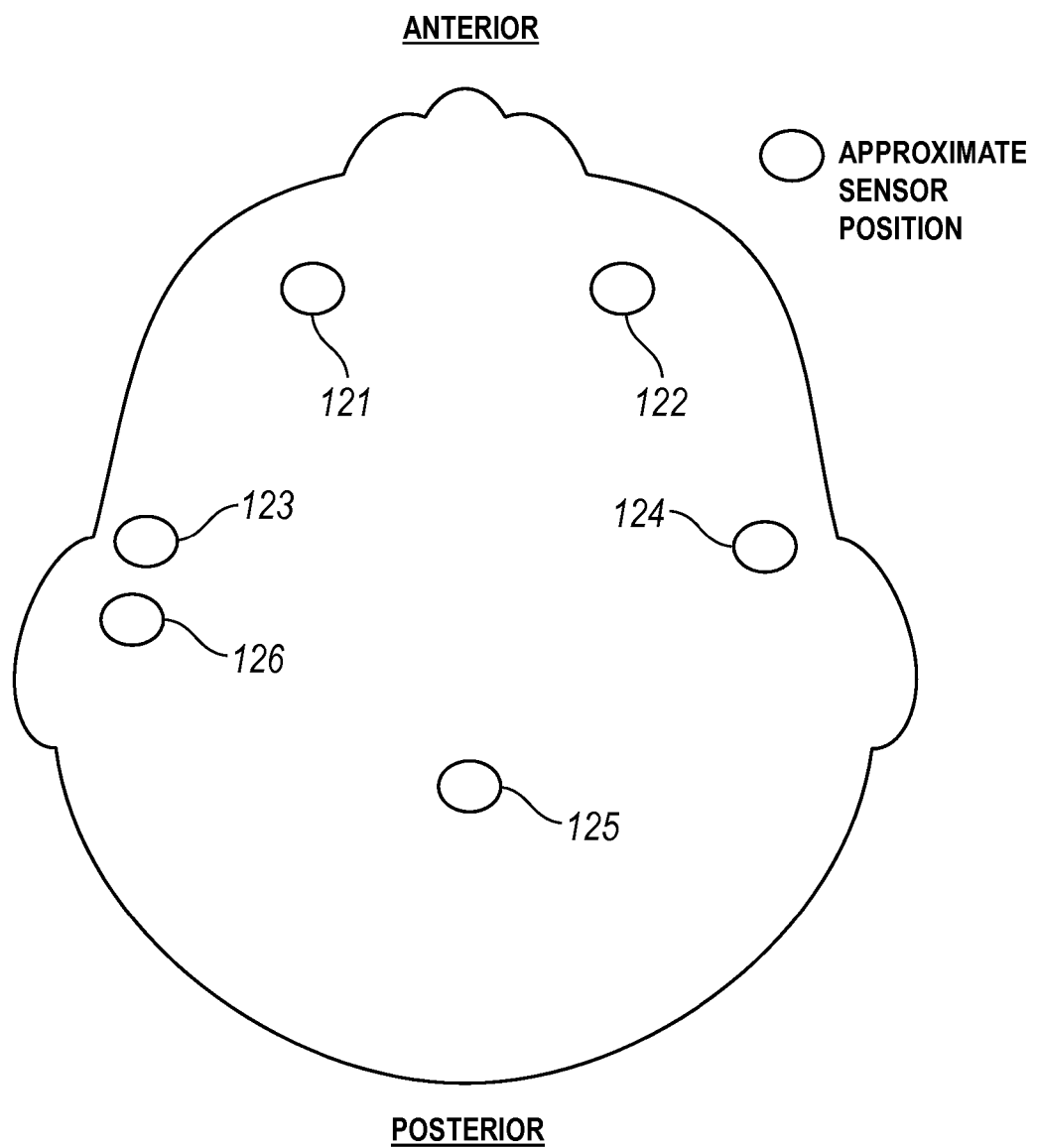
FIG. 1C depicts a specific example of sensor positions provided by an embodiment of a system for detecting and measuring biosignals.

In one example, as shown in FIG. 1C, the set of sensors 120 comprises a first anterior frontal sensor 121, a second anterior frontal sensor 122, a first temporal lobe sensor 123, a second temporal lobe sensor 124, a central sensor 125, and a common mode sensor 126, wherein the common mode sensor 126 is configured to provide a reference signal. In the example, each sensor in the set of sensors 120 provides a single channel for signal detection, is characterized by a frequency bandwidth from above DC to 80 Hz, and is characterized by a nominal voltage of 10-100 microvolts; however, the full dynamic range of the electronics system in the example can accommodate 5 millivolt signals to accommodate large electromyographic signals (e.g., eye blinks, clenched jaw signals). Furthermore, in the example, the set of sensors 120 is configured to be non-adjustable in location (i.e., not adjustable in gross location, while cooperating with a housing to maintain contact at an appropriate location on the user), while providing adequate signal detection from multiple regions of the brain. In other variations, the set of sensors 195 can comprise any suitable number of sensors in any suitable configuration for detecting biosignals from the user, examples of which are described in U.S. Pat. No. 7,865,235, and U.S. Publication Nos. 2007/0066914 and 2007/0173733 with regard to EEG signals detected from a user's brain.

Figure 2:
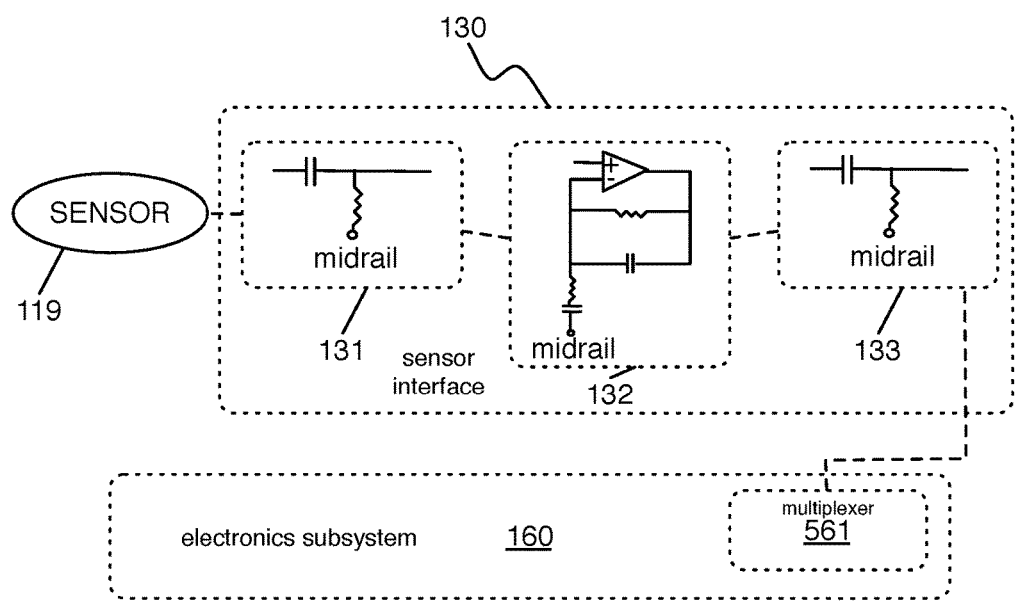
FIG. 2 depicts an variation of a sensor interface in an embodiment of a system for detecting and measuring biosignals.

The set of sensor interfaces 130 functions to preprocess a set of signals from the set of sensors 120, prior to further processing and transmission at the electronics subsystem 160. In particular, the set of sensor interfaces 130 can function to amplify signals received using the set of sensors 120, and/or to adjust an output of the set of sensor interfaces 130 relative to a voltage level governed by an element of the electronics subsystem 160, as described below. Preferably, each sensor interface of the set of sensor interfaces 130 comprises a pre-gain alternating current (AC) coupling and level shift 131 coupled to an amplifier 132, and a post-gain AC coupling and level shift 133. The pre-gain AC coupling and level shift function to block direct current (DC) signals and to shift signals from the set of sensors 120 closer to a mid-rail voltage provided by a mid-rail generator of the electronics subsystem 160, in order to provide an approximately equal dynamic range with each polarity. As such, the pre-gain AC coupling and level shift 131 preferably comprise a resistor-capacitor network, as shown in FIGS. 1A and 2, which also functions as a high-pass filter with a low signal frequency (e.g., 0.159 Hz) that effectively blocks DC signals (i.e., 0 Hz signals). However, variations of the set of sensor interfaces can omit a level shift. The resistor-capacitor network is preferably coupled to an amplifier 132, whose feedback network (e.g., feedback resistor) gives it a suitable gain (e.g., 50) to amplify biosignals received using the set of sensors 120. Furthermore, in order to limit a high frequency response and to avoid excessive phase shift due to the amplifier 132, the feedback resistor can be coupled to a capacitor in parallel to create a low-pass filter (e.g., a low pass filter that starts high-frequency roll-off at 80 Hz). The amplifier can additionally or alternatively be coupled to a capacitor in series with a gain resistor, in order to prevent amplification of DC signals (i.e., 0 Hz signals). A high gain resulting from amplification of a biosignal will result in an offset at the amplifier output; thus, the post-gain AC coupling and level shift 133 functions to restore signal balance to the mid-rail voltage provided by a mid-rail generator of the electronics subsystem 160. In one variation, the post-gain AC coupling and level shift 133 comprises a second high-pass resistor-capacitor network, but can comprise any other suitable element(s). The set of sensor interfaces 130 can additionally or alternatively comprise any suitable element or combination of elements (e.g., filters, etc.) for preprocessing of signals from the set of sensors 120.

The set of sensor interfaces 130 is preferably coupled to the set of sensors 120 proximal to a set of sensor-user interfaces defined between the set of sensors and the body of the user, as shown in FIG. 1A. Coupling of the set of sensor interfaces 130 proximal to the set of sensors can function to facilitate mitigation of electrostatic interference and/or accommodation of high input impedances due, for instance, to the use of dry/semi-dry sensor materials in the set of sensors 120 and/or non-ideal coupling (e.g., partially broken coupling, discontinuous coupling) of the set of sensors 120 to the user. As such, each sensor in the set of sensor interfaces 130 is preferably positioned immediately adjacent to one or more corresponding sensors of the set of sensors, in order to facilitate pre-processing of signals received at the set of sensors. In one such variation, a sensor interface of the set of sensor interfaces 130 can be mounted directly to a corresponding sensor of the set of sensors 120, and in communication with the electronics subsystem 160 by way of the set of arms of the housing, which can facilitate reduction of electrostatic interference and/or accommodate a high input impedance attributed to use of a dry/semi-dry sensor material. In one specific example of this variation, a unit comprising a pre-gain AC coupling and level shift coupled to an input of an amplifier and a post-gain AC coupling and level shift coupled to an output of the amplifier can be directly coupled to an output of a sensor of the set of sensors 120, in order to provide a sensor interface immediately adjacent to a corresponding sensor of the set of sensors 120. In alternative variations, the set of sensor interfaces 130 can be coupled to the set of sensors at any suitable distance from the set of sensors. In one such alternative variation, one or more sensor interfaces of the set of sensor interfaces 130 can be coupled to (e.g., mounted to, incorporated with) the electronics subsystem 160, as described below, with any other suitable electrical coupler(s) from the set of sensor interfaces 130 to the set of sensors 120.

The set of sensor interfaces 130 is preferably coupled to the set of sensors 120 in a one-to-one manner, such that each sensor of the set of sensors 130 has a corresponding sensor interface of the set of sensor interfaces 120. However, in some variations, multiple sensors can be configured to feed a signal into one sensor interface of the set of sensor interfaces 130 in a many-to-one manner for instance, in variations wherein multiple sensors provide a single channel for signal detection. Alternatively, the set of sensor interfaces 130 can have any other suitable number and/or coupling configuration relative to the set of sensors 120.

The biosignal sensor subsystem 110 can also comprise or be coupled to additional sensor subsystems configured to capture data related to other biological processes of the user and/or the environment of the user. As such, the biosignal sensor subsystem can comprise any one or more of: optical sensors to receive visual information about the user's environment, global positioning system (GPS) elements to receive location information relevant to the user, audio sensors to receive audio information about the user's environment, temperature sensors, sensors to detect MEG impedance or galvanic skin response (GSR), sensors to measure respiratory rate, and/or any other suitable sensor.

1.2 System—Housing

The housing 140, as shown in FIGS. 1A-1B, is preferably worn at a head region of a user, and functions to house and/or protect elements of the system. The housing 140 can additionally function to provide the system to a user in an aesthetic and/or wearable form factor. Additionally or alternatively, the housing 140 can function to maintain contact between the set of sensors 120 of the biosignal sensor subsystem 110 and the user by allowing some level of deformation of the housing 140, and is preferably configured so as to not disrupt a user's use of his/her eyes, nose, ears, and mouth. As such, the housing 140 preferably does not obstruct the user's vision, smell, and/or hearing, and does not interfere with the user's use of his/her jaw. Furthermore, the housing 140 can facilitate positioning and/or coupling of the set of sensors 120 to the user, for instance, in passing the set of sensors 120 through the user's hair to provide suitable contact with the user's scalp. In one variation, the housing comprises a set of arms 145 configured to maintain contact between the set of sensors 120 and the user, and a set of sensor couplings 150 configured to enhance wearability and to protect the set of sensors 150. The housing is preferably opaque, but can alternatively be transparent/translucent or can be modular and comprise transparent portions (e.g., around the eyes, so as to not disrupt the user's vision). The housing is preferably composed of an elastically deformable (e.g., not brittle), but stiff material, such that the housing is elastically deformable to provide adequate contact between sensors and the user, but is still able to provide adequate mechanical support for elements of the system 100. The housing 140 can thus comprise any suitable material or combination of materials (e.g., polymer, plastic, metal), and can be processed by any suitable manner (e.g., injection molding, forming, casting, etching, machining) to allow for reversible deformation while still providing mechanical support for elements of the system 100.

The housing 140 is preferably configured to ensure contact between the set of sensors 120 of the biosignal sensor subsystem 110 and a suitable region of the user's body, and is preferably further configured to substantially surround sensors of the set of sensors 120, aside from portions intended to contact the user at sensor-user interfaces defined between the set of sensors 120 and the body of the user. In variations comprising dry/semi-dry sensors (e.g., dry sensors saturated with a nonvolatile fluid), the housing 140 can be configured to define an exposed area for each sensor of the set of sensors 120, and to substantially cover areas of sensor pads not defining the exposed areas. Such a configuration can mitigate loss of fluid (e.g., non-volatile fluid) from sensors of the set of sensors 120, while still providing adequate contact for signal conduction. In variations comprising sensor pads saturated with fluid (e.g., dry sensors with a nonvolatile fluid, wet hydrated sensors), the housing 140 can further define an opening (e.g., a top-up hole) configured to allow the addition of fluid to compensate for fluid depletion from a sensor of the set of sensors 120 during extensive usage of the biosignal sensor subsystem no. Alternatively, the housing can omit a top-up hole, and additional fluid can be supplied at an exposed sensor area or other point of access to a sensor pad of the set of sensors 120. Additionally or alternatively, the housing 140 can incorporate, surround, or be coupled to a sensor fluid reservoir 142 coupled to a fluid distribution module 143, that can be configured to release fluid in response to sensor pad fluid depletion. In variations comprising sensor pads saturated with fluid, the housing 140 is preferably resistant to the fluid and/or the sensor pad materials (e.g., resistant against material degradation, material corrosion, etc.), and is also configured to provide mechanical support for the sensor pad, in particular, for sensor pads composed of compliant (e.g., soft, deformable) materials.

The set of arms 145 of the housing function to provide a mechanically robust connection between the housing 140 and the set of sensors 120 coupled to the housing, and to stabilize positions for the set of sensors 120 interacting with the user. The set of arms 145 can further function to establish an electrical connection between a sensor of the set of sensors 120, and an electronics subsystem 160 of the system 100. The set of arms 145 is preferably of unitary construction with the housing 140, but can alternatively be physically coextensive with the housing 140 or coupled to the housing 140 in any other suitable manner. Furthermore, a subset of the set of arms 145 can be of unitary construction with the housing 140, and another subset of the set of arms can be configured to couple to the housing 140 in a modular manner. Similar to the housing, the set of arms 145 is preferably composed of an elastically deformable (e.g., not brittle), but stiff material, such that the set of arms 145 is elastically deformable to provide adequate contact between sensors and the user, but is still able to provide adequate mechanical support for the set of sensors 120. Additionally, the housing 140, along with the set of arms 145, is preferably configured to provide firm, but not excessive, contact pressure at each location where a sensor interfaces with the user's body, thus enhancing user comfort. Each arm in the set of arms 145 is further preferably individually deflectable to allow independent adjustment of each sensor coupled to an arm as the user moves during daily activities. Independent deflection thus allows an individual sensor to maintain contact with the user as the user moves, and can further function to prevent motion of one sensor from leading to decoupling of other sensors in contact with the user's body. However, each arm in the set of arms 145 can alternatively be defined by any other suitable aspect ratio and/or place a sensor at a desired sensor location in any other suitable manner. In one example, each arm in the set of arms 145 comprises an elastically deformable metallic contact strip overmolded with a flexible plastic material, which provides an adequate spring force for maintaining sensor coupling with the user, and for providing electrical connections between sensors and the electrical subsystem 160. In other variations, the set of arms can be composed of any other suitable material or combination of materials.

Figure 3A:
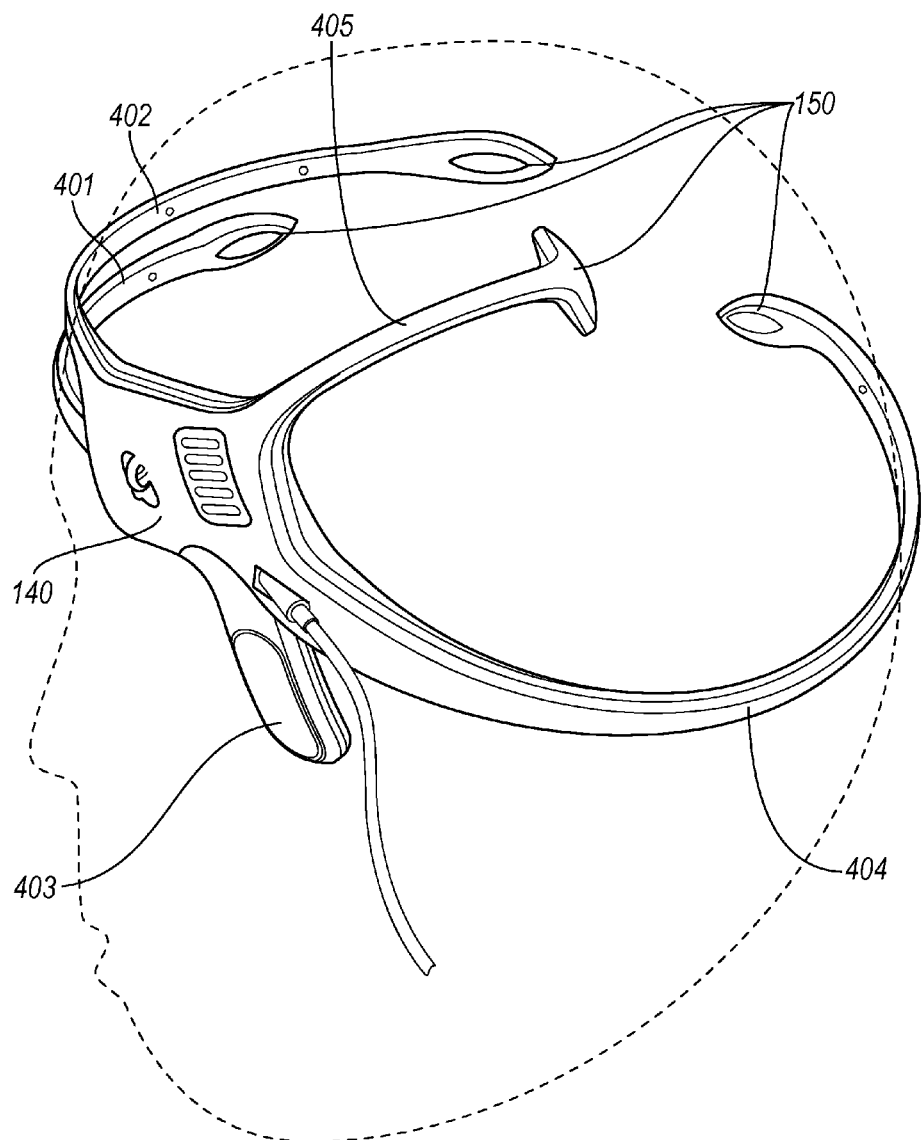
FIG. 3A depicts a first specific example of a system for detecting and measuring biosignals.
Figure 3B:
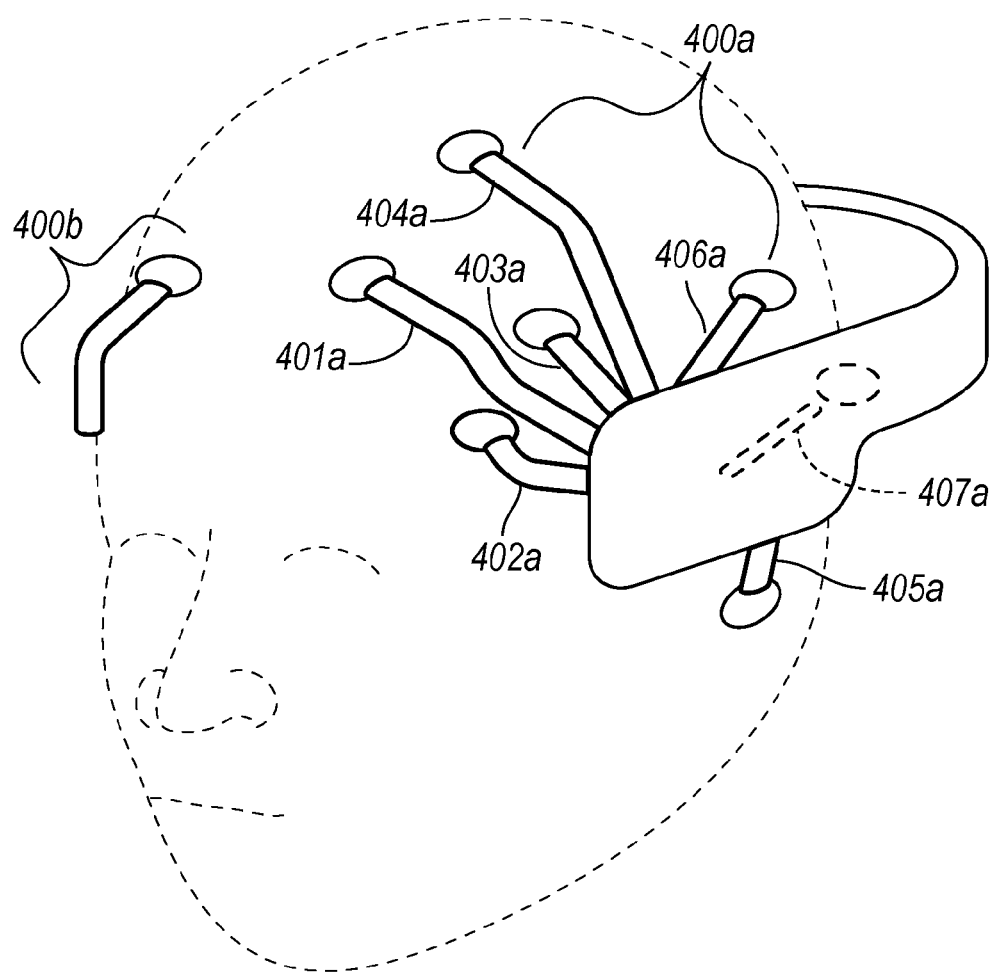
FIG. 3B depicts a second specific example of a system for detecting and measuring biosignals.

The set of arms 145 is also preferably configured to facilitate conveyance and/or penetration of the set of sensors 120 through layers of a user's hair. As such, each arm in the set of arms 145 is preferably defined by a high aspect ratio (e.g., high length to width ratio), as shown in FIGS. 1B, 3A, and 3B, that allows the set of arms 145 to "comb" through the user's hair to place a sensor at a suitable sensor location. Also shown in FIGS. 1B and 3A, each arm preferably extends from the housing 140, curves about the user's skull, and terminates at a sensor coupling configured to place a sensor at a desired location on the user. As such, the set of arms 145 preferably contribute to a housing 140 that lacks symmetry; however, variations of the housing 140 can alternatively be symmetric about any suitable axis or plane relative to the body of the patient (e.g., symmetry about a coronal plane, symmetry about a sagittal plane, etc.). In line with a housing configuration that preferably does not obstruct the user's vision, smell, and/or hearing, the set of arms 145 is preferably configured to avoid blocking the user's eyes, ears, nose, and mouth. In one variation, each of the set of arms 145 can be configured to extend from a single portion of the housing (e.g., a portion of the housing configured to be positioned proximal a temporal bone of the user, a portion of the housing configured to be positioned proximal a parietal bone of the user, a portion of the housing configured to be positioned proximal the occipital bone of the user, a portion of the housing configured to be positioned proximal the frontal bone of the user, etc.). Alternatively, the set of arms 145 can be configured to extend from multiple portions of the housing in a symmetric or an asymmetric manner relative to a plane (e.g., sagittal plane, coronal plane) or axis defined through the user's body.

In a specific example, as shown in FIGS. 1B and 3A, the set of arms 140 comprises a first arm 401 configured to extend from the housing 140 proximal a first temporal bone of the user and to curve toward the frontal bone of the user to terminate, at a distal end, at an anterior portion of the frontal bone of the user; a second arm 402 configured to extend from the housing 140 proximal the first temporal bone of the user and to curve toward the frontal bone of the user to terminate, at a distal end, at a lateral portion of the frontal bone of the user; a third arm 403 configured to extend from the housing 140 proximal the first temporal bone of the user and to pass toward an inferior portion of the first temporal bone of the user, to terminate, at a distal end, at a portion of the first temporal bone of the user; a fourth arm 404 configured to extend from the housing 140 proximal the first temporal bone of the user and to curve about the user's occipital bone to terminate, at a distal end, at a second temporal bone of the user; and a fifth arm 405 configured to extend from the housing 140 proximal the first temporal bone of the user and to curve about the user's parietal bone to terminate, at a distal end, at a superior portion of the parietal bone of the user (e.g., proximal the sagittal suture of the parietal bone). The set of arms can alternatively be configured in any other suitable manner to facilitate placement of the set of sensors 120 at desired sensor locations.

In another specific example, as shown in FIG. 3B, the set of arms 140 comprises a first subset of arms 400a and a second subset of arms 400b, wherein the first subset of arms 400a and the second subset of arms 400b form a pair of arm subsets configured to be positioned symmetrically at contralateral portions of the head of the user. In this specific example, the first subset of arms 400a comprises a first arm 401a configured to extend from the housing 140 proximal a first temporal bone of the user and to curve toward the frontal bone of the user to terminate, at a distal end, at an anterior portion of the frontal bone of the user; a second arm 402a configured to extend from the housing 140 proximal the first temporal bone of the user and to curve toward the frontal bone of the user to terminate, at a distal end, at a lateral portion of the frontal bone of the user, superior to the distal end of the first arm 401a; a third arm 403a configured to extend from the housing 140 proximal the first temporal bone of the user and to curve toward the frontal bone of the user to terminate, at a distal end, at a lateral portion of the frontal bone of the user, lateral and inferior to the distal end of the first arm 401a; a fourth arm 404a configured to extend from the housing 140 proximal the first temporal bone of the user and to curve toward the frontal bone of the user to terminate, at a distal end, proximal to a junction between the frontal bone, the parietal bone, and the first temporal bone of the user; a fifth arm 405a configured to extend from the housing 140 proximal the first temporal bone of the user and to terminate, at a distal end, at a portion of the first temporal bone of the user; a sixth arm 406a configured to extend from the housing 140 proximal the first temporal bone of the user and to curve toward the parietal bone of the user to terminate, at a distal end, at a posterior lateral portion of the parietal bone of the user; and a seventh arm 407a configured to extend from the housing 140 proximal the first temporal bone of the user and to curve toward the occipital bone of the user to terminate, at a distal end, at a posterior lateral portion of the occipital bone of the user. In this specific example, the second subset of arms 400b mirrors the first subset of arms 400a about the sagittal plane of the user. As such, this specific example of the housing includes a first pair of frontal lobe sensors, a second pair of frontal lobe sensors, a third pair of frontal lobe sensors, a fourth pair of frontal lobe sensors, a pair of temporal lobe sensors, a pair of parietal lobe sensors, and a pair of occipital lobe sensors, positioned by the first and the second subsets of arms 400a, 400b. Variations of either specific example can additionally or alternatively include sensors for sampling of a midrail voltage provided by an embodiment of the electronics subsystem 160, as described below.

The set of sensor couplings 150 is preferably coupled to distal ends of the set of arms 145 of the housing 140, and functions to house the set of sensors 120, facilitate electromechanical coupling of the set of sensors to the electronics subsystem 160 of the system 100. The set of sensor couplings can further enable modularity and/or reusability of elements of the system 100. Preferably, each sensor coupling of the set of sensor couplings 150 is configured to be reversibly coupled to the housing 140 and/or the set of arms 145; however, the set of couplings 150 can alternatively be configured to be non-reversibly coupled to or to be of unitary construction with the housing in non-modular variations of the system 100. In some variations, the set of sensor couplings 150 comprises sensor couplings that are individually pivotable and/or translatable, in order to facilitate maintenance of contact between a sensor and the user, and/or to allow readjustment of a sensor location; however, in other variations, the set of sensor couplings 150 can comprise one or more sensor couplings that are substantially fixed in orientation and/or position (e.g., relative to other features of the housing 140). As described earlier, the set of sensor couplings 150 can define openings (e.g., openings facing the body of the user upon coupling of the system 100 to the user) that expose the sensor pads of the set of sensors 120 (i.e., to enable coupling of the sensors to the user). Additionally, each sensor coupling in the set of sensor couplings 150 can comprise an adhesive layer and/or elastomeric elements that further enhance coupling of a sensor to the user. Each sensor coupling in the set of sensor couplings 150 also preferably comprises an electrical contact configured to electrically couple a sensor pad, through a metallic contact strip of an arm of the set of arms 140, to an electronics subsystem 160 to enable biosignal detection and processing, as described in further detail below. In some variations, each sensor coupling in the set of sensor couplings 150 can be characterized by a profile that tapers to a point, in order to facilitate passage of the housing through and around the user's hair; however, in other variations, each sensor coupling can be characterized by any other suitable profile or geometry.

Figure 4A:
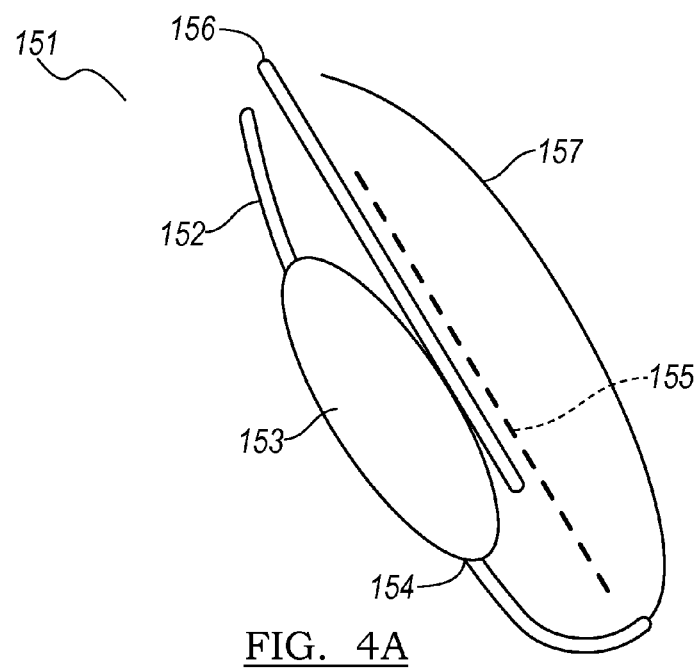
FIGS. 4A-4C depict an embodiment and two views of and a first example of a portion of a system for detecting and measuring biosignals, respectively.
Figure 4B:
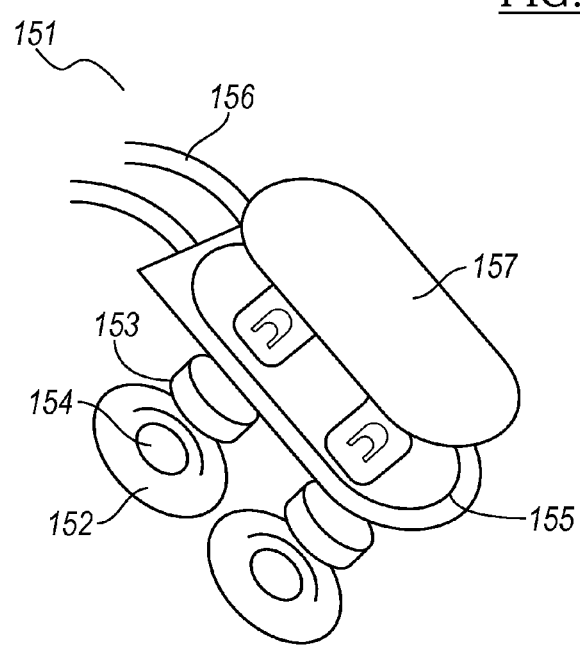
Figure 4C:
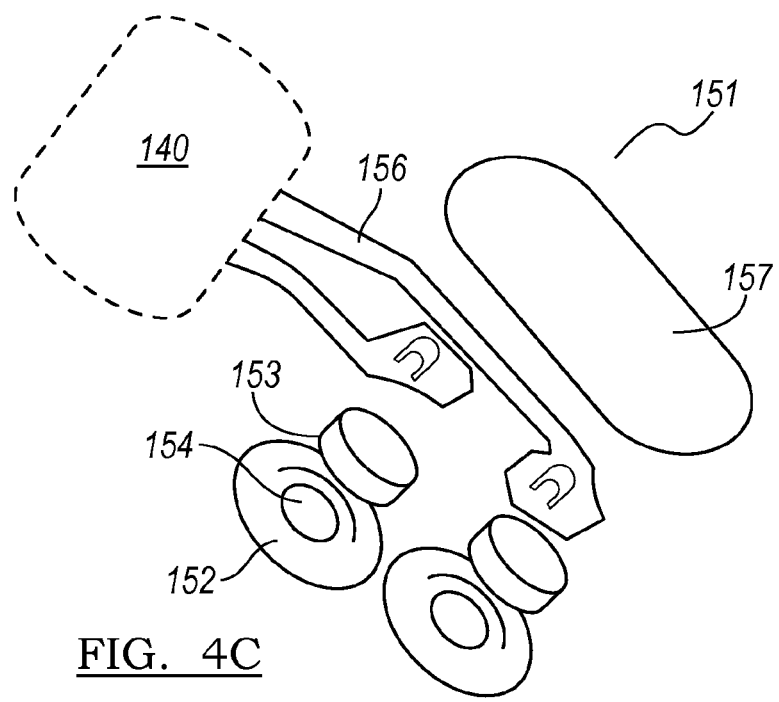

In specific examples, as shown in FIGS. 4A-4C, the set of sensor couplings 150 can implement a snap-fit mechanism configured to provide mechanical support to the sensor pad material, provide openings that expose portions of the sensor pad material for coupling to the user, and also couple the sensor pad material to electrical contacts, configured to electromechanically couple to metallic contact strips of the set of arms. In the specific examples, a sensor coupling 151 comprises a cap 152 configured to position and seat a dry sensor pad 153 while exposing a portion of the sensor pad that contacts the user through an opening 154 in the cap 152 facing the body of the user upon coupling of the system 100 to the user. In the specific examples, the sensor coupling further comprises an intermediate region 155 configured to couple to the cap 152 by a snap-fit mechanism and to couple the sensor coupling 151 to an electrical contact 156 (that couples to a metallic contact strip of an arm of the set of arms 140), such that the dry sensor pad 153 is sandwiched between the cap 152 and the electrical contact 156, and the cap 152 couples to the intermediate region 155 by the snap-fit mechanism. In the specific examples, the sensor coupling further comprises a top layer 157 configured to fully seal the sensor coupling 151 at a second surface directly opposing a surface of the sensor pad 153 coupled to the user, wherein the top layer 157 couples to the intermediate region 155 by a snap-fit mechanism. In the specific examples, a single sensor coupling 151 can comprise one or multiple units comprising a cap 152, a sensor pad 153, an electrical contact 156, an intermediate region 155, and a top layer 157. Furthermore, in variations of the specific examples, mechanisms in addition to or alternative to snap-fit mechanisms can be implemented in the set of sensor couplings 150. For instance, the set of sensor couplings can implement any one or more of: a magnetic coupling mechanism, an adhesive coupling mechanism, a bonding mechanism (e.g., chemical-based, heat based, etc), a hook-and-loop fastening mechanism, a bolting fastening mechanism, and any other suitable coupling mechanism. In some variations, an interface between an electrical contact 156 and sensor pad 153 can be additionally or alternatively enhanced by coating, painting or electroplating the electrical contact 156 with and/or constructing the sensor pad 153 with, a non-polarizable contact material (e.g., Ag/AgCl) that provides coupling to an electrolyte fluid exuded by the sensor pad 153. Additionally or alternatively, providing non-polarizable contact by way of more of more of the electrical contact 156 and/or the sensor pad 153 can be implemented using any other suitable contact enhancement(s) (e.g., gold plating to minimize corrosion, unplated materials).

Figure 4D:
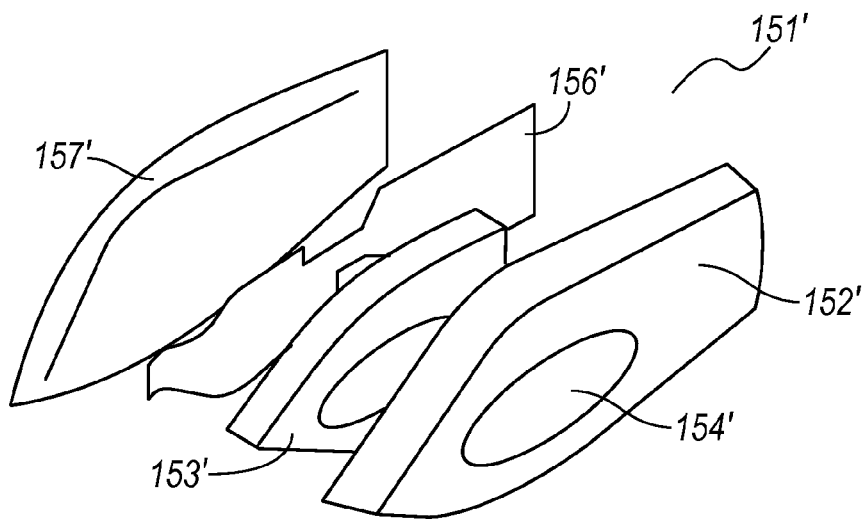
FIG. 4D depicts a second example of a portion of a system for detecting and measuring biosignals.

In another specific example, as shown in FIG. 4D, a sensor coupling 151' of the set of sensor couplings 150 can comprise a cap 152' configured to position and seat a dry sensor pad 153' while exposing a portion of the sensor pad 153' that contacts the user, through an opening 154' in the cap 152' facing the body of the user upon coupling of the system 100 to the user. In these specific examples, the sensor coupling 151' further includes an electrical contact 156' (that couples to a metallic contact strip of an arm of the set of arms 140) directly contacting the dry sensor pad 153' without an intermediate region. In these specific examples, the sensor coupling 151' further comprises a top layer 157' configured to fully seal the sensor coupling at a second surface directly opposing a surface of the sensor pad 153' coupled to the user, wherein the top layer 157' couples to the cap 152' region by a snap-fit mechanism. As such, the dry sensor pad 153' is sandwiched between the cap 152' and the electrical contact 156', and the cap 152' couples to the top layer 157' by the snap-fit mechanism without an intermediate region. The sensor coupling assembly in these examples, comprising a cap 152', a sensor pad 153', an electrical contact 156', and a top layer 157', thus provides support for a sensor pad of the set of sensors 120, while providing a means for electromechanically coupling the sensor to an arm of the set of arms 145 in a modular manner. Furthermore, in variations of the specific examples, mechanisms in addition to or alternative to snap-fit mechanisms can be implemented in the set of sensor couplings 150. For instance, the set of sensor couplings can implement any one or more of: a magnetic coupling mechanism, an adhesive coupling mechanism, a bonding mechanism (e.g., chemical-based, heat based, etc), a hook-and-loop fastening mechanism, a bolting fastening mechanism, and any other suitable coupling mechanism.

In variations and specific examples of the set of sensor couplings 150, one or more sensor coupling of the set of sensor couplings 150 is preferably reversibly coupleable to the housing 140, in order to support modularity and/or replaceability of aspects of the system 100. As such, in some examples, each sensor coupling of the set of sensor couplings 150 can reversibly couple to a distal end of a corresponding arm of the set of arms 140 of the housing by a coupler (e.g., electromechanical coupler) that provides mechanical support and enables electrical conduction between an electrical contact 156 of a sensor coupling and the electronics subsystem 160. The coupler(s) can implement any one or more of: magnetic coupling elements, adhesive coupling elements, mechanical snap-fit coupling elements, mechanical press-fit coupling elements, and any other suitable type of coupling element. The set of sensor couplings 150 can, however, comprise any other suitable mechanism for housing sensor pads of the set of sensors 120, and can provide coupling of a sensor to the user and/or the electronics subsystem 160s in any other suitable manner.

1.3 System—Electronics Subsystem

The electronics subsystem 160 functions to provide regulated power to the system 100, to facilitate detection of biosignals from the user by incorporating signal processing elements, to couple to additional sensors for comprehensive collection of data relevant to the user and/or the biosignals being detected, and to enable transmission and/or reception of data by the system 100. In one embodiment, as shown in FIG. 1A, the electronics subsystem 160 comprises a digital electronics subsystem 510 configured to facilitate noise isolation in the system 100 and an analog electronics subsystem 560 configured to couple to the digital electronics subsystem 110 by an inter-board connection 559, wherein the biosignal sensor subsystem 110 is coupled to the electronics subsystem (e.g., analog electronics subsystem 560) by way of electrical contacts 156 of sensor couplings of the set of sensor couplings 150. The electronics subsystem 160 is preferably configured to separate "noisy" elements from "quiet" elements in order to provide greater sensitivity in signal detection and/or measurement. As such, the digital electronics subsystem 510 (comprising elements producing noise above a threshold level) is preferably distinct from the analog electronics subsystem 560 (comprising quiet elements), as described in greater detail below. The system 100 can, however, be configured in any other suitable alternative manner that provides sufficient sensitivity for detection and/or measurement of biosignals.

1.3.1 Digital Electronics Subsystem

Figure 5:
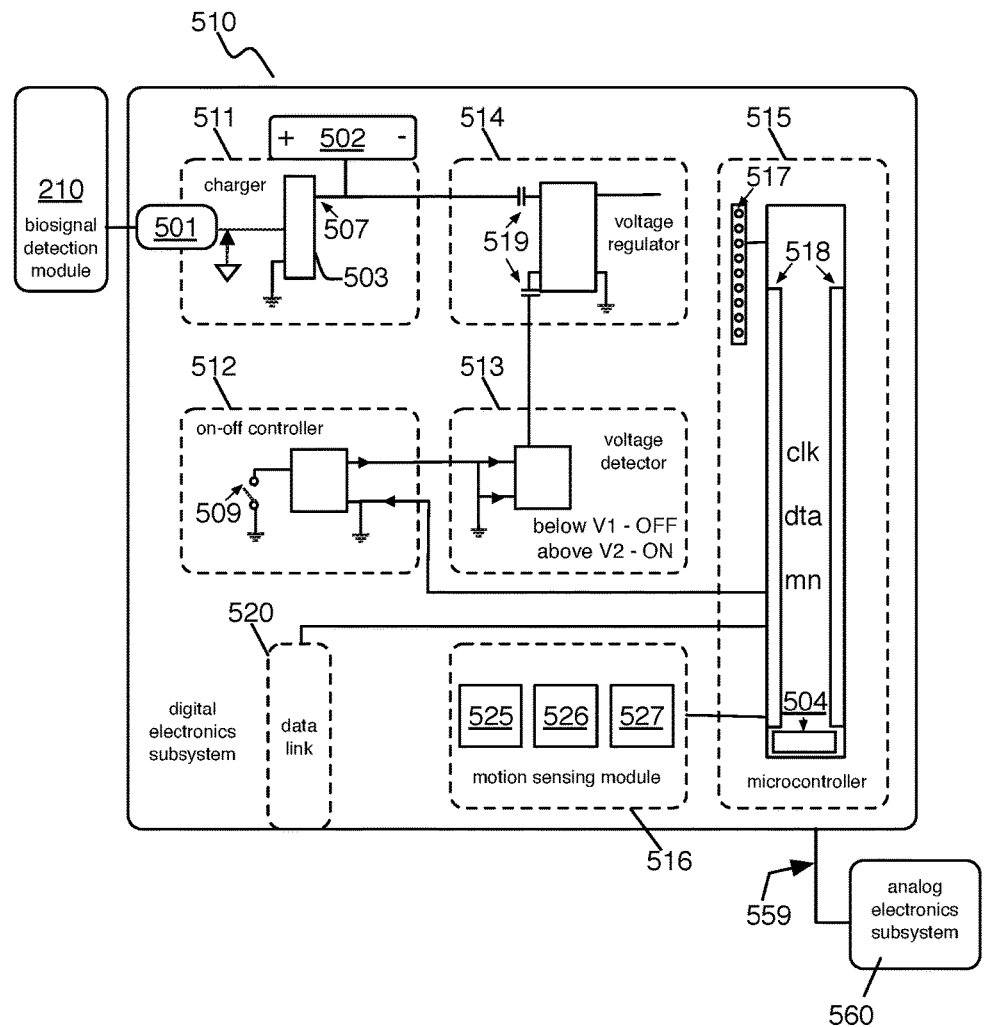
FIG. 5 depicts an embodiment of a digital electronics subsystem of an embodiment of a system for detecting and measuring biosignals.

As shown in FIGS. 1A and 5, the digital electronics subsystem 510 preferably comprises a charger 511, an on-off controller 512, a voltage detector 513, a voltage regulator 514, a microcontroller 515, a motion sensing module 516, and a data link 520, and functions to separate noisy elements from quiet elements to provide greater sensitivity in detecting and measuring biosignals. A specific example of the digital electronics subsystem 510, as shown in FIG. 1A comprises a digital printed circuit board configured to provide a substrate and connections for a charger 511, an on-off controller 512, a voltage detector 513, a voltage regulator 514, a microcontroller 515, a motion sensing module 516, and a data link 520.

The charger 511 is preferably coupled to a charger input 501 and a battery 502, and functions to provide regulated electrical power to the system 100 and to allow power storage for the system 100. The charger input 501 is preferably a wired connection coupled to the voltage regulator 514, which functions to restrict a voltage at the charger input 501 to a limiting range of voltages. The charger input 501 thus functions to receive a supply voltage, and to provide a form of electrical safety for the system 100. In some variations, the charger input 501 can comprise a stereo connection and/or a universal serial bus (SUB) connection configured to couple the electronics subsystem 160 to an external computing device (e.g., personal computer, lap top, etc.). The charger input 501, can, however, comprise any other suitable connection (e.g., a custom input). In a specific example, the charger input 501 comprises a 3.5 mm stereo socket and couples to a voltage regulator 514 configured to limit the voltage at the charger input 501 to a range of –0.7V to 6.5V. As such, the charger input 501 is configured to couple to a voltage suppressor diode (6.5V, 400 W transient voltage suppressor diode), and in variations of the specific example, can be configured to couple to a fuse (e.g., 200 mA holding-current, 500 mA trip-current PTC fuse) coupled to the voltage suppressor diode. In variations of the specific example, the fuse can be configured to open if a supply voltage is greater than 6.5V or if the supply voltage is reversed (e.g., the supply voltage provides –0.7V) and can be a resettable fuse, such that the fuse is configured to reset (initially to a high resistance and then to a nominal resistance after the fuse has equilibrated) after the fuse has "cooled down". The fuse can, however, be a non-resettable fuse or any other suitable fuse, and some variations of the system 100 can altogether omit a fuse. Furthermore, the charger input can, in other variations, be a wireless connection in variations wherein the system 100 is configured to charge by another means, such as inductive charging.

The charger 511 couples to the charger input 501 and preferably comprises a charger controller 503 (e.g., BQ24060DRC charger controller that can withstand voltages of up to 26V for up to 87 hours) coupled to a bulk capacitor (e.g., a 4.7 uF bulk capacitor for frequencies below 1 kHz) and a bypass capacitor (e.g., a 100 nF bypass capacitor for frequencies above 1 kHz). Variations of the charger controller 503 connections can alternatively omit coupling to one or more of the bulk capacitor and the bypass capacitor. The charger controller 503 is preferably directly coupled to the battery 502 by an output pin, which passes energy directly to the battery 502. In a specific example, the output pin of the charger controller 503 is configured to pass pulsed charge energy to the battery 502, with a capacitor, preferably having a capacitance value (e.g., 1 uF) less than that of an input capacitor at the charger controller input, coupled to ground in order to provide stability during various modes of use. The charger controller 503 can also comprise pin controls for indicators (e.g., LEDs on the analog electronics subsystem) that indicate when charging is in progress and/or when charging is complete. In a specific example, LED indicators can have a brightness determined by current-limit resistors, wherein a forward voltage of 2V at an LED and an output low saturation voltage of 0.5V of the charger integrated circuit results in a voltage drop of 2.5V at a corresponding current-limit resistor. The current-limit resistors can, however, comprise any suitable voltage value to modulate a brightness of an LED indicator (or an intensity of any other suitable indicator). The charger controller 503 can also comprise a timer output configured to couple to a timer resistor to ground, which determines a maximum charging time (e.g., 10 hours) for the battery 502. In some variations of the specific example, the charger controller 503 can further comprise a charge current regulator 506, which in a variation of the specific example is implemented by a grounded resistor connected to a current set pin on the charger controller 503 and is configured to set the charge current to 94 mA (e.g., to provide a reasonable charging time without overheating the battery). In some variations, the charger controller 503 can also comprise an open drain output to inhibit system 100 operation during charging; however, the system 100 can alternatively be configured to allow operation during charging.

The battery 502, as shown in FIG. 5, is preferably a rechargeable lithium-ion polymer battery (e.g., specified at 3.7V at 480 mA/hour, with a charged voltage of 4.2V and a discharged voltage of 3.0V) but can alternatively comprise any other suitable rechargeable battery (e.g., nickel-cadmium, metal halide, nickel metal hydride, or lithium-ion). However, other embodiments of the system 100 can be configured to omit recharging functionality, and can thus comprise a non-rechargeable battery (e.g., alkaline battery) that can be replaceable to enhance modularity in the system 100. The voltage of the battery 502 is preferably detected in real-time at a battery input 507 of the charger controller 503, wherein a capacitor (e.g., 1 uF) is coupled between the battery input 507 and the charge current regulator of the charger controller 503 to provide stability; however, the voltage of the battery 502 can be detected in any other suitable manner. The temperature of the battery can be detected within the battery, at a thermal detection input 508 of the charger controller 503, or in any other suitable manner.

The on-off controller 512 functions to turn the system 100 on and off, and is preferably coupled to a momentary switch 509 and to the voltage detector 513. In some variations, the on-off controller is configured to hold the system 100 off, rather than force it on; however, the on-off controller 512 can be configured to turn off and/or turn on the system 100 in any other suitable manner (e.g., force the system off, force the system on, hold the system off, hold the system on). In a specific example, as shown in FIG. 2A, the on-off controller 512 is a MAX16054AZT controller with a clear pin, such that a command from a digital signal processing integrated circuit (e.g., the microcontroller 515) can turn the system 100 off through the clear pin. In the specific example, a diode of the on-off controller 512 pulls a low voltage detection input into the voltage detector 513 below a minimum detection threshold, which holds the system 100 off; however, when the momentary switch 509 is turned on, an output of the on-off controller 512 coupled to the low voltage detection input goes high, reverse biasing the low voltage detection input, such that the voltage detector 513 is able to monitor the voltage of the battery 502.

The voltage detector 513 is preferably coupled to the battery 502 and to the on-off controller 512, and functions to detect a voltage of the battery 502, in order to ensure proper function of the system 100. Preferably, the voltage detector 513 prevents unintended lapses in system 100 operation due to a low battery voltage. Furthermore, the voltage detector 513 can function to facilitate maintenance of a battery 502 (e.g., lithium-ion polymer battery) of the system 100 above a certain discharge voltage (e.g., 3V for lithium-ion polymer batteries), in order to prevent lapses in proper function of the system 100. The voltage detector 513 preferably cooperates with the on-off controller 512, as described earlier, to maintain the voltage to the voltage regulator 514 within a certain voltage range. As such, the voltage detector 513 can be configured to operate in a first state upon detection of a lower limiting voltage (e.g., a lower limiting voltage configured to trigger a system 100 shut-off), and to operate in a second state upon detection of a higher limiting voltage (e.g., a higher limiting voltage configured to set a voltage at which the system 100 is configured to turn on). In one example, as shown in FIG. 2A, if the voltage detector 513 detects that the battery voltage falls below 3.4V, the system 100 is configured to shut off. Furthermore, in the specific example, the battery voltage must be above 3.5V, as detected at the voltage detector 513, in order for the system 100 to turn on. In the example, when the battery voltage is detected to be above 3.5V, an output of the voltage detector 513 feeds into the voltage regulator 514, to provide a 3.3V voltage line for the system 100. The voltage detector 513 can, however, function to facilitate modulation of a voltage output using any other suitable conditions for system 100 operation.

The voltage regulator 514 functions to provide a regulated voltage power output to other system elements, and preferably supplies power to both the digital electronics subsystem 510 and the analog electronics subsystem 560. However, the voltage regulator 514 can alternatively be configured to provide regulated or unregulated power to a portion of the digital electronics subsystem 510 and/or the analog electronics subsystem 560. The voltage regulator 514 and the voltage detector 513 preferably cooperate, such that the voltage regulator 514 is turned on by a pull-up resistor at a sufficient voltage level (3.5V), and power is held off at the voltage regulator 514 upon detection of an insufficient voltage (e.g., below 3.4V). The voltage regulator 514 is preferably a low drop-out voltage regulator, and in one example, as shown in FIG. 2A, is configured to output 3.3V to both the digital electronics subsystem 510 and the analog electronics subsystem 560. In the example, the voltage regulator 514 is configured to couple to low equivalent series resistance bypass capacitors 519 (e.g., having less than 1 Ohm resistance) at both an input and an output of the voltage regulator 514, in order to facilitate noise reduction.

The microcontroller 515 is a programmable module, is configured to couple to elements of the digital electronics subsystem 510 and/or the analog electronics subsystem 560, and functions to control the system 100. The microcontroller 515 is thus preferably coupled to a programming connector 517, and preferably comprises a set of programming pins 518 configured to enable programming of different functionalities of the microcontroller 515. The microcontroller 515 can be configured to facilitate wired and/or wireless handling of signals associated with biosignal data. In one example, as shown in FIG. 2B, the microcontroller 515 has three programming pins 518, associated with a clock, a data handling function, and a main function. In the example, the clock comprises a crystal oscillator circuit operating at 16 MHz; however, the microcontroller can be configured to operate with any other suitable clock element(s). In some variations, the microcontroller 515 can also comprise a serial signal output line 504 (e.g., to the charger input 501 stereo connection, to SUB connection, to another external connection, etc.), such that wired output of data from the microcontroller 515 is also enabled. In an example, the serial signal output line 504 is coupled to the 3.5 mm stereo socket of the charger 511, comprises a transient-voltage suppression (TVS) diode and a current limit resistor, and enables wired output of data to an external module. The microcontroller 515 can be configured to perform at least a portion of the method described in U.S. Pat. No. 7,865,235, and/or U.S. Publication Nos. 2007/0066914 and 2007/0173733, which are each incorporated in their entirety by this reference. In other variations, the microcontroller can be additionally or alternatively configured to enable or perform a portion of the methods described in U.S. application Ser. Nos. 13/903,806, 13/903,832, and 13/903,861, each filed on 28 May 2013, which are each incorporated in their entirety by this reference. In some variations, the microcontroller 515 can be preconfigured to perform a given method, with the system 100 configured such that the microcontroller 515 cannot be reconfigured to perform a method different from or modified from the given method. Furthermore, data sampling parameters can be governed using the microcontroller 515, and can additionally or alternatively be implemented in firmware associated with the system 100. However, in other variations of the system 100, the microcontroller can be reconfigurable to perform different methods.

The motion sensing module 516 functions to detect an orientation of the system 100, and is preferably coupled to the microcontroller 515 to enable detection of system orientation and/or motion of a user coupled to the system 100. The motion sensing module 516 preferably provides full acceleration detection (i.e., detection of acceleration in all directions) and absolute position sensing as a 9-axis motion sensor; however, the motion sensing module 516 can alternatively provide any other suitable type of acceleration detection (e.g., acceleration detection along a single axis) and/or position sensing (e.g., relative position sensing). The motion sensing module 516 can comprise any one or more of a gyroscope 525, an accelerometer 526, and a magnetometer 527 in order to facilitate motion and/or position sensing. In variations of the motion sensing module 516 comprising a gyroscope 525, the gyroscope 525 can be a 2-axis gyroscope, a 3-axis gyroscope, as shown in FIG. 2B, or any other suitable gyroscope for orientation detection. In variations of the motion sensing module 516 comprising an accelerometer 526, the accelerometer can be a single-axis accelerometer or a multi-axis accelerometer (e.g., an X-Y accelerometer) in order to enable detection of acceleration in one or more coordinate directions. In variations of the motion sensing module 516 comprising a magnetometer 527, the magnetometer can operate as a compass based upon detection of a direction of a magnetic field (e.g., the Earth's magnetic field) at any point in space. The magnetometer 527 can be a vector magnetometer that enables measurement of vector components of a magnetic field and/or can be a total field magnetometer that enables measurement of a magnitude of a vector of a magnetic field. Furthermore, the magnetometer 527 can be an absolute magnetometer that measures an absolute magnitude using physical constants of a magnetic sensor of the magnetometer, or can be a relative magnetometer that measures a magnitude of a magnetic field relative to an uncalibrated baseline. In some variations, the magnetometer can enable measurement of variations in a magnetic field (e.g., as in a variometer). Furthermore, the magnetometer 527 preferably provides an adequate sample rate (readings per unit time), bandwidth to track changes in magnetic field parameters, resolution, drift, absolute error, thermal stability, sensitivity, low amount of noise, and a sufficiently limited dead zone (e.g., angular region of magnetometer in which the magnetometer measurements are untrustworthy).

Preferably, the motion sensing module 516 comprises non-stationary elements that are configured to be used while in motion, such that motion and/or position of the user/system 100 are enabled while the user is in motion. However, one or more elements of the motion sensing module 516 can be configured to be stationary. In one variation, all elements of the motion sensing module 516 are integrated within the housing 140 of the system 100, proximal the head-region of the user, in order to enable precise detection of motion and position of the head of the user. However, the elements of the motion sensing module 516 can alternatively be positioned relative to the user in any other suitable manner. Furthermore, variations of the motion sensing module 516 can comprise one or more instances of any of the gyroscope(s) 525, the accelerometer(s) 526, and the magnetometer(s) 527, for instance, to provide expanded motion/position detection or redundancy of elements in the system 100. The system 100 can, however, comprise any additional or alternative sensing units (e.g., GPS elements) and/or can be configured in any other suitable manner.

The data link 520 is preferably coupled to the microcontroller 515, and functions to transmit an output of at least one element of the digital and/or the analog electronics subsystems 510, 560 to a mobile device or other computing device (e.g., desktop computer, lap top computer, tablet, smartphone, health tracking device) for further processing and/or analysis. Preferably, the data link 520 is a wireless interface, as shown in FIG. 2C. In a first variation, the data link 520 can include a Bluetooth module that interfaces with a second Bluetooth module included in the mobile device or external element, wherein data or signals are transmitted by the data link to/from the mobile device or external element over Bluetooth communications. In an example of the first variation, the Bluetooth module comprises a 32 MHz crystal oscillator for radiofrequency transmissions, a 32.768 kHz crystal oscillator for standby operations, and common mode choke configured to reduce noise being conducted back into the system 100. In variations of the data link 520 comprising a Bluetooth module, the Bluetooth module is preferably a low-energy Bluetooth module that reduces power used of the system 100 during data transfer processes. The data link 520 of the first variation can additionally or alternatively implement other types of wireless communications, such as 3G, 4G, radio, or Wi-Fi communication. In the first variation, data and/or signals are preferably encrypted before being transmitted by the data link 520, in particular, for applications wherein the data and/or signals comprise medical data. For example, cryptographic protocols such as Diffie-Hellman key exchange, Wireless Transport Layer Security (WTLS), or any other suitable type of protocol can be used. The data encryption may also comply with standards such as the Data Encryption Standard (DES), Triple Data Encryption Standard (3-DES), or Advanced Encryption Standard (AES). The data link 520 can, however, additionally or alternatively comprise a wired connection (e.g., a universal serial bus connection to an external computing device). In one example, of a wired connection, the data link 520 can include a fully isolated universal serial bus (SUB) connection that is injected molded and sealed within the housing 140, in order to provide a connection to the digital electronics subsystem 510.

The data link 520 can further facilitate transmission of data at a desired rate and resolution. Furthermore, data transmission can be configurable to provide data through the data link 520 at adjustable rates/resolutions. Providing data at a desired rate and resolution can be enabled based upon adjustment of data packet rate and/or structure, and transmission can occur continuously, semi-continuously, or intermittently through the data link 520. In one specific example, substantially continuous data transfer can be facilitated using a low-energy Bluetooth module, as described above, which allows data transmission while limiting energy usage. In variations wherein the data is provided at an adjustable rate/resolution, the rate and/or resolution can be based upon variations in signal parameters detected from the user. For instance, time of day and/or type of activity (e.g., detected using other elements of the system) can be used to provide boundary conditions for setting the adjustable rate/resolution of data transmission.

The digital electronics subsystem 510 can additionally or alternatively comprise any other suitable element or combination of elements for providing (un)regulated power to the system 100, handling signals detected by the system 100, and/or controlling elements of the system 100. For instance, some variations of the digital electronics subsystem 510 can include a storage module configured to provide local storage (e.g., at a storage module incorporated with the housing 140 of the system 100) and/or remote storage (e.g., at an external computing device, server-based storage, cloud-based storage, etc.) of data generated using the system 100. In examples of local storage, the system 100 can incorporate a storage card (e.g., a Secure Digital card, a memory stick, etc.) within the housing 140 and coupled to the digital electronics subsystem 510 for local data storage. The digital electronics subsystem 510 can, however, include any other elements that facilitate biosignal detection and/or handling.

1.3.2 Analog Electronics Subsystem

Figure 6:
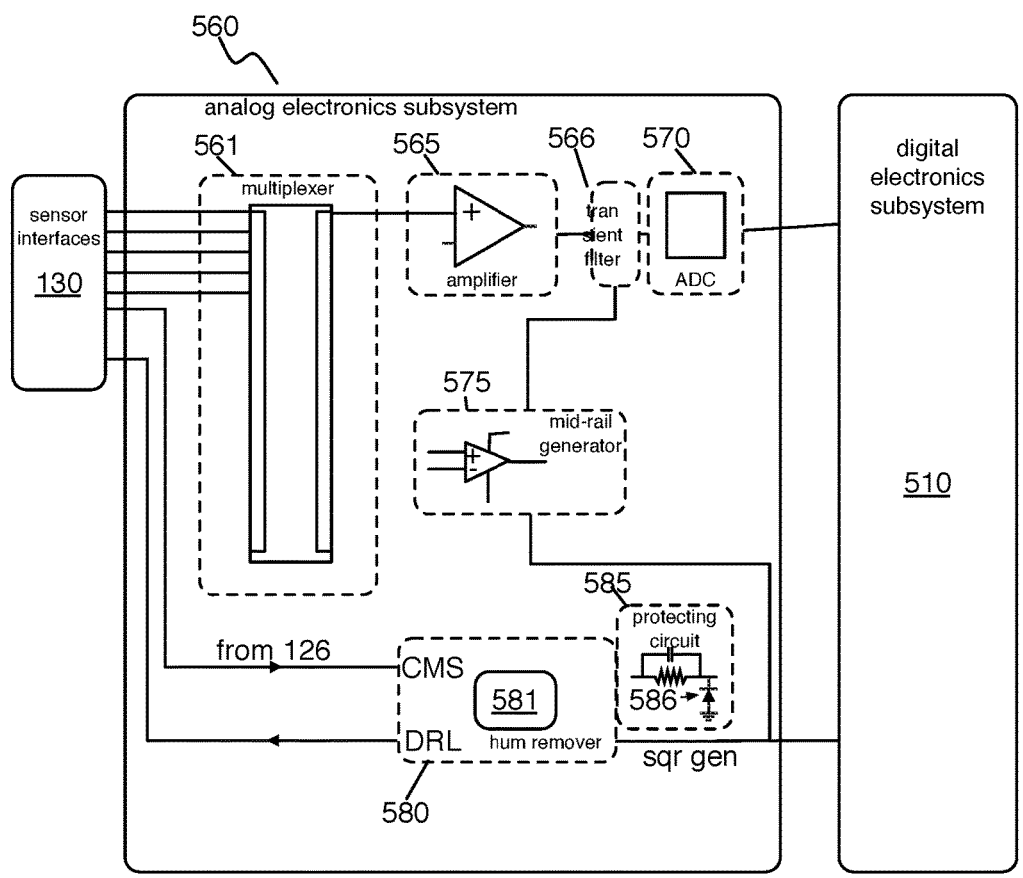
FIG. 6 depicts an embodiment of an analog electronics subsystem of an embodiment of a system for detecting and measuring biosignals.

As shown in FIGS. 1A and 6, the analog electronics subsystem 560 preferably comprises a multiplexer 561, an amplifier 565 coupled to an output of the multiplexer 561, an analog-to-digital converter (ADC) 570 coupled to an output of the multiplexer 561, a mid-rail generator 575 configured to generate a half-rail voltage from a supply voltage, a hum remover 580, and a protecting circuit 585, and functions to transition signals from the biosignal sensor subsystem 110 into digital data. The analog electronics subsystem 560 can further comprise a set of LEDs, as described earlier, which can indicate proper function and/or dysfunction of elements of the system 100. The analog electronics subsystem 560 is preferably "quiet" (e.g., minimizes noise interference with signals from the biosignal sensor subsystem and comprises elements producing noise below a threshold level) and, as such, is preferably distinct from the digital electronics subsystem 510. As such, the system 100 preferably comprises an inter-board connection 559 that maintains at least partial separation between the digital and the analog electronics subsystems 510, 560, but enables some communication between the digital and the analog electronics subsystems 510, 560. In other variations, the digital and the analog electronics subsystems 510, 560 can be non-distinct, and may not be connected by an inter-board connection 559. A specific example of the analog electronics subsystem 160, as shown in FIG. 4B, comprises an analog printed circuit board configured to serve as a substrate and to facilitate connections for a multiplexer 561, an amplifier 565, an analog-to-digital converter (ADC) 570, a mid-rail generator 575, a hum remover 580, and a protecting circuit 585.

The analog electronics subsystem 560 can comprise discrete components, or can alternatively comprise dedicated single-chip modules. Furthermore, the analog electronics subsystem 160 can comprise off-shelf components or custom integrated circuits configured to perform signal processing (e.g., signal conditioning, signal amplification). Preferably, the analog electronics subsystem 560 provides adequate connection characteristics to accommodate high input impedances associated with the sensors of the biosignal sensor subsystem 110 (e.g., dry skin sensors), and in specific examples, is configured to support input impedances in the range of 1 mega-ohm to 1 giga-ohm resulting from use of dry/semi-dry sensors. However, the analog electronics subsystem 560 can alternatively accommodate any suitable range of input impedances.

The inter-board connection 559 is preferably an electrical interface that allows power transmission between the digital and the analog electronics subsystems 510, 560, and some signal transmission between the digital and the analog electronics subsystems 510, 560, in order to facilitate isolation of noise-generating elements of the electronics subsystem 160. In one example, the inter-board connection 559 comprises a pin-strip coupling including a first header and a second header to provide sufficient rigidity between the printed circuit boards of the digital and the analog electronics subsystems 510, 560. In the example, the inter-board connection 559 is configured to interface with the digital electronics subsystem 110 at a J148 and a J149 interface, and configured to interface with the analog electronics subsystem 560 at a J280 and a J281 interface. The inter-board connection 559 can, however, include any other suitable connection, or can be omitted in variations of the system 100 with more closely integrated digital and analog electronics subsystems 510, 560.

The multiplexer 561 is preferably configured to receive multiple signals from the set of sensors 120 through a set of sensor interfaces 130 of the biosignal sensor subsystem no, and to forward the multiple signals received at multiple input lines in a single line at the analog electronics subsystem 560. The multiplexer 561 thus increases an amount of data that can be transmitted within a given time constraint and/or bandwidth constraint. The number of input channels to the multiplexer 561 is preferably greater than or equal to the number of output channels of the biosignal sensor subsystem 110, wherein a $2^n$ relationship exists between the number of input lines and the number of select lines of the multiplexer 561 (e.g., a multiplexer of $2^n$ input lines has n select lines, which are used to select an input line to output). However, the multiplexer 561 can have any other suitable relationship between the number of input lines into the multiplexer and the number of output lines of the multiplexer. Furthermore, the multiplexer 561 can have any other suitable number of select lines provided by any other suitable channel scan selection mechanism. In a specific example, the biosignal sensor subsystem 110 comprises five channels corresponding to five sensors of the set of sensors 120 with a spare channel, and the multiplexer 561 comprises eight input lines (e.g., the multiplexer is an 8:1 multiplexer) with three parallel select lines. In the specific example, the multiplexer 561 has a low-voltage switch on resistance of 2 ohms. The multiplexer 561 can include a post-multiplexer gain 562 (e.g., 10) in order to reduce capacitance values of front-end amplifiers coupled to the multiplexer 561; however, the multiplexer 561 can alternatively not include any gain producing elements. In some variations, the multiplexer 561 can additionally or alternatively include high frequency and/or low frequency limiting elements.

As noted in Section 1.1 above, the set of sensor interfaces 130 is preferably coupled to the set of sensors 120 proximal to a set of sensor-user interfaces defined between the set of sensors and the body of the user, in order to facilitate mitigation of electrostatic interference and/or accommodation of high input impedances due, for instance, to the use of dry sensor materials in the set of sensors 120 and/or non-ideal coupling (e.g., partially broken coupling, discontinuous coupling) of the set of sensors 120 to the user. However, the set of sensor interfaces 130 can alternatively be coupled to the electronics subsystem 160 and coupled proximal to the analog electronics subsystem 560, in other variations of the system. In one example, a unit comprising a pre-gain AC coupling and level shift coupled to an input of an amplifier and a post-gain AC coupling and level shift coupled to an output of the amplifier can be electrically coupled to an output of a sensor of the set of sensors 120, wherein the unit is positioned proximal to or integrated with analog electronics subsystem 560, at a location distant from the set of sensors 120. As such, in these variations, the set of sensor interfaces 130 can be coupled to the set of sensors at any suitable distance from the set of sensors 120. Similar to the variations in which the set of sensor interfaces 130 is coupled proximal to the set of sensors 120, the set of sensor interfaces 130 is preferably coupled to the set of sensors 120 in a one-to-one manner in variations wherein the set of sensor interfaces 130 is at a location distant from the set of sensors 120, such that each sensor of the set of sensors 130 has a corresponding sensor interface of the set of sensor interfaces 120. However, in some variations, multiple sensors can be configured to feed a signal into one sensor interface of the set of sensor interfaces 130 in a many-to-one manner for instance, in variations wherein multiple sensors provide a single channel for signal detection. Alternatively, the set of sensor interfaces 130 can have any other suitable number and/or coupling configuration relative to the set of sensors 120.

The amplifier 565 is preferably coupled to the multiplexer 561, and functions to amplify a signal output of the multiplexer 561. The amplifier 565 can also be coupled to a transient filter 566 configured to suppress inter-channel switching transients resulting from channel switching using the multiplexer 561. In one example, as shown in FIGS. 3A and 3B, the amplifier 565 is configured to amplify an output signal of the multiplexer 561 by a gain factor of 3, and is coupled to a transient filter 566 configured to dampen transients resulting from voltage potentials (e.g., voltage potentials of 3V) between consecutively selected multiplexer channels, thus reducing the settling time and improving the sampling rate of the multiplexer 561. The system 100 can comprise any suitable number of amplifiers 565, depending upon the configuration of the amplifier(s) relative to other elements (e.g., the multiplexer 561) of the analog electronics subsystem 560. In one variation, the amplifier 565 is placed after the multiplexer 561 in order to amplify a single output line of the multiplexer 561. In another variation, a set of amplifiers is placed before the multiplexer 561, in order to amplify multiple input channels into the multiplexer 561. In yet another variation, the analog electronics subsystem 560 comprises amplifiers before and after the multiplexer, in order to amplify input and output lines of the multiplexer 561.

The ADC 570 is preferably coupled to the multiplexer 561 through the amplifier 565, and functions to convert analog signals into digital signals. The ADC 570 can be characterized by any suitable number of bits, and in a specific example, is characterized by 16-bits, with only 14-bits being used. The ADC 570 can also comprise an internal voltage reference. In a manner similar to that of the amplifier(s), the system 100 can comprise any suitable number of ADCs 570 depending upon configuration relative to other elements of the analog electronics subsystem 560.

Figure 7A:
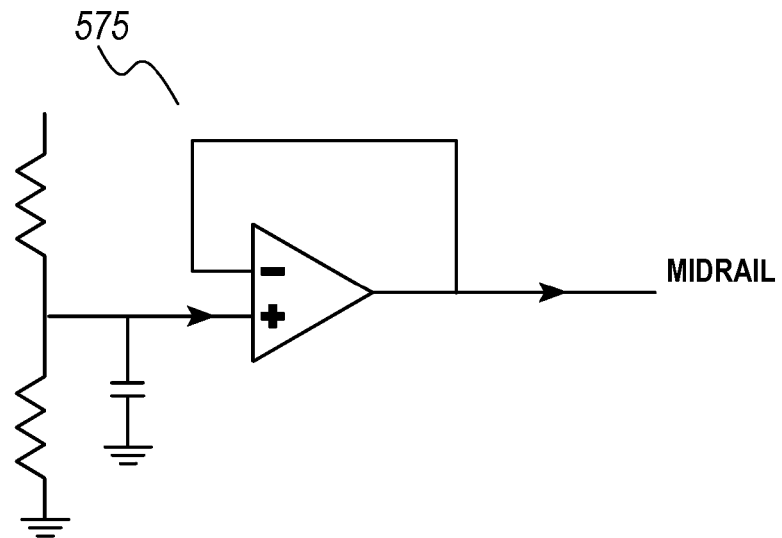
FIGS. 7A and 7B depict two specific examples of a mid-rail generator in an embodiment of a system for detecting and measuring biosignals.
Figure 7B:
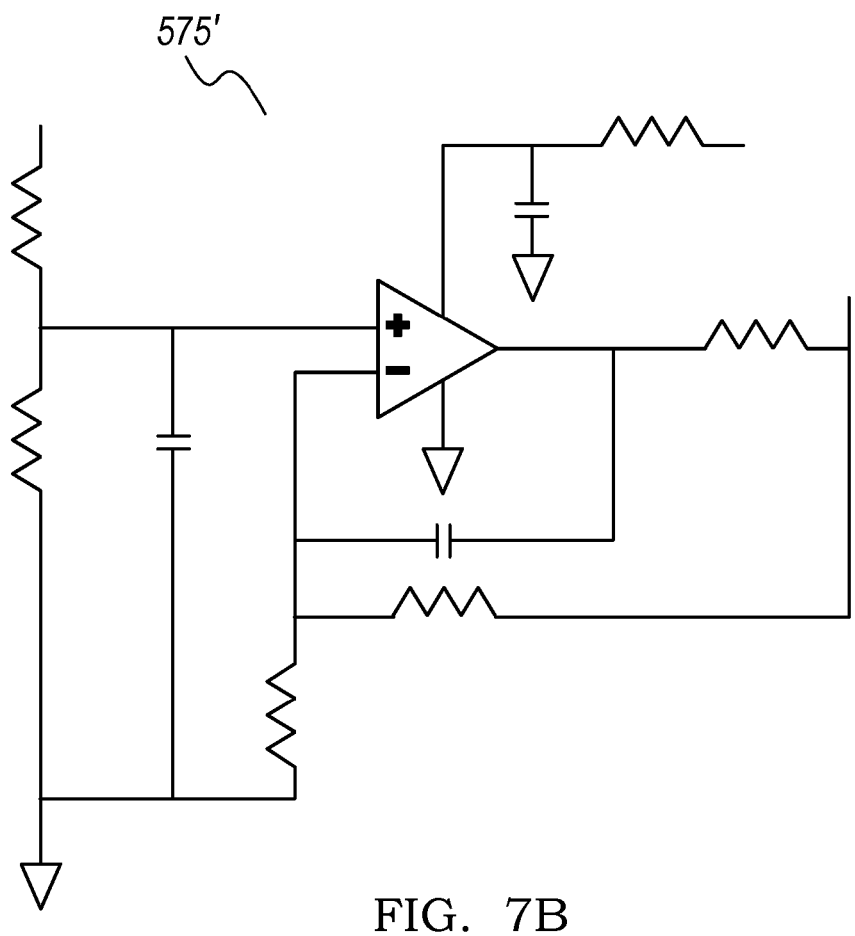

The mid-rail generator 575 functions to provide dual polarity or split-supply operation of the system 100, by providing at least a second voltage line of the electronics subsystem 160. In one example, as shown in FIG. 7A, the mid-rail generator is implemented by dividing a voltage supplied at 3.3V, and buffering a resulting half-voltage to form the mid-rail generator 575. In another example, as shown in FIG. 7B, the mid-rail generator comprises an operational amplifier configured to generate the mid-rail voltage line. In this example, the non-inverting input is set to ⅓ of a supply voltage of 0.75V, and the operational amplifier has gain factor of 2 yielding 1.5V at the output of the operational amplifier. In other variations, the analog electronics subsystem 560 can additionally or alternatively comprise a mid-rail generator configured to provide a voltage supply at any other suitable voltage level to increase the available supply polarities provided by the system 100. As such, variations of the analog electronics subsystem 560 can be configured to provide any suitable number of voltage supplies, each having a specified voltage level.

The hum remover 580 is configured to accommodate a user's body potential and to mitigate effects of interfering signals (e.g., electromagnetic radiation) received through the user's body. As such, the hum remover 580 functions to removal signal interference (e.g., from main frequency hum) by sampling a local ambient signal (e.g., from a common mode sensor 126 of the set of sensors 120) and feeding the local ambient signal back to a skin surface of the user, proximal to a system-user interface defined between the user and the system 100, as a driven right leg (DRL) signal. In one variation, as shown in FIG. 6, the hum remover 580 can comprise an attenuator 581 configured to divide a voltage output provided by the digital electronics subsystem 510, and in a specific example is configured to divide a 3.3V square wave (or any other suitable wave) from the digital electronics subsystem 510 by 4000 to give a 400 mV signal centered about a mid-rail voltage supplied by the mid-rail generator 575. In this variation, the hum remover 580 also couples to a common mode sensor 126 (e.g., skin sensor) of the biosignal sensor subsystem 110 configured to monitor the user's body potential, wherein the common mode sensor 126 is protected by a transient voltage suppressor (TVS) diode. In this variation, the output of an attenuator 581 can be transmitted through an integrator (e.g., an integrator with a response time of 1.6 kHz determined by a series resistor and capacitor) to a high impedance current-limit resistor and back to the common mode sensor 126 to form the DRL signal (i.e., a composite signal formed by a square wave centered about the mid-rail voltage, integrated with a signal from the common mode sensor 126). Furthermore, the hum remover 580 in this variation is configured to inject a signal sampled from the common mode sensor 126 into a biosignal detection path (e.g., a path defined at the user's scalp in contact with the biosignal sensor subsystem 110), such that the contact potential of each biosignal sensor of the set of sensors 120 can be assessed in real time to facilitate user setup. Preferably, the amplitude of the signal injected into the biosignal detection path is detectable at a minimum voltage resolution of detection by the system, after transmission through skin of the user and while accounting for signal attenuation outside of an amplifier pass band (e.g., of 20 µV) of the system; however, the amplitude of the signal can be configured in any other suitable manner. The amplitude of such a signal sampled from the common mode sensor 126 can additionally be used to normalize a detected biosignal to a predefined level, in order to improve a quantitative accuracy of a biosignal measurement. Furthermore, the frequency of the square wave integrated with the signal from the common mode sensor is preferably selected based upon parameters of noise in the system 100.

Preferably, the hum remover 580 is configured to superimpose a square wave with a signal from the common mode sensor 126, wherein the frequency of the square wave is at a higher frequency than a range of interest (i.e., a frequency range) for bioelectrical (e.g., EEG) signals from the brain of a user, but within a range of detection governed by one or more amplifiers of the system associated with the hum-remover/square wave generator. However, the frequency of the square wave can alternatively be lower than the range of interest, or within the range of interest in variations. In specific examples, the frequency of the square wave can range from 80-150 Hz, and in one specific example, can be 128 Hz. As such, an amplitude of a detected signal at the frequency of the square wave, for each sensor channel of the system, can be used to estimate a quality of contact for each sensor and can additionally or alternatively be used to permit compensation of the amplitude of the detected signal in a quantitative manner to account for losses due to obstructed or poor contact between a sensor and the user. The hum remover 580 can, however, can comprise any other configuration for mitigating effects of interfering signals detected and/or transmitted by the user's body.

The protecting circuit 585 functions to protect elements (e.g., front-end operational amplifiers) of the analog electronics subsystem 560 from static discharge and/or an over-voltage condition, by way of at least one transient voltage suppressor (TVS) diode 586 connected to ground. The TVS diode(s) 586 preferably match(es) a voltage provided by a voltage regulator 514 (e.g., a 3.3V supply provided at the digital electronics subsystem 510), but can alternatively be rated at any other suitable voltage. Additionally, the TVS diode(s) 586 of the protecting circuit are preferably uni-polar, to prevent a high negative transient voltage (e.g., −5V) from being passed to an element (e.g., front-end operational amplifier) of the analog electronics subsystem 560. In one example, the TVS diode 586 is a uni-polar 3.3V diode configured to clamp at −1.0V and +4.3V to provide sufficient protection. Additionally, the TVS diode 586 in the example is configured with a shunt capacitance to ground of 105 pF, but can be configured with any other suitable shunt capacitance. The protecting circuit 585 is preferably integrated with the hum remover 580, and can further be integrated with any subset of the set of sensor interfaces 130, as described in Section 1.1 above. Variations of the examples of the protecting circuit 585 can, however, be configured in any other suitable manner to mitigate effects of static discharge, to prevent an over-voltage condition at the electronics subsystem 160, and/or prevent a high negative transient voltage (e.g., −5V) from being passed to an element (e.g., front-end operational amplifier) of the analog electronics subsystem 560.

The analog electronics subsystem 560 can additionally or alternatively comprise any other suitable combination of elements for handling biosignal detection, biosignal detection, biosignal processing, and/or biosignal transmission, in a manner that provides sufficient sensitivity and reduces signal interference by noisy elements. In one variation, the analog electronics subsystem 560 can further comprise a common mode filter (e.g., common mode choke), configured to remove noise from the power supply elements, the microcontroller 515 and/or the data link 520 of the digital electronics subsystem 510.

Variations of the electronics subsystem 160, including the digital electronics subsystem 510 and/or the analog electronics subsystem 560, can be integrated with any other suitable sensors configured to detect biosignals from the user's body and/or signals from the user's environment. For instance, a supplementary sensing module 590 can be configured to detect and feed signals into any suitable element (e.g., the multiplexer 561) of the electronics subsystem 160 for further processing and analysis. In variations, the supplementary sensing module 590 can include sensors and modules configured to detect any one or more of: electrooculography (EOG) signals, electromyelography (EMG) signals, and any other suitable bioelectrical signals. The supplementary sensing module 590 can also include sensors and modules configured to detect non-bioelectrical signals including any one or more of: signals related to body temperature, signals related to cerebral blood flow (CBF), signals derived from magnetic resonance imaging (e.g., fMRI data), mechanical signals (e.g., mechanomyographs, signals recorded from an accelerometer), chemical signals (e.g., blood oxygenation), and any other signals obtained from or related to biological tissue, biological processes, or mental processes of the user. Furthermore, the supplementary sensing module 590 can include sensors and/or modules configured to detect any other suitable physiological and/or environmental signal (e.g., temperature, air quality, light intensity, etc.) relevant to the user. The biosignal detection module 210 can, however, comprise any other suitable element(s), suitable number of elements to provide sensor redundancy, or combination of element(s). Furthermore, any or all of the sensors and modules described in the embodiment and variations above can further be implemented at a mobile device or other electronic device of the user.

1.4 Other System Elements

As shown in FIG. 1A, the system 100 can further comprise an external charging module 210 configured to provide power from an external source to the system 100. The external charging module 210 functions to supply power to the system 100 through the charger input 501. Preferably, the external charging module 210, in combination with the charger 511 and charger input 501, adhere to relevant regulatory standards. The external charging module 210 is preferably suitable for use in multiple countries, and is characterized by a suitable voltage range, current range, frequency, and connection type. The external charging module 210 can be specified at any suitable voltage and current, and in a specific example is specified at 5V+0.25V and 120 mA. In some applications involving use of the system 100 during charging, the external charging module 210 can comprise a medical-grade power supply with sufficient isolation (e.g., 6 kV of isolation). In one example, the external charging module 210 comprises a male pin configured to couple to a 3.5 mm stereo socket of the charger input; however, the external charging module 210 can comprise any other suitable connection to the charger input.

In variations wherein the battery 502 of the system is rechargeable, the external charging module 210 can additionally or alternatively comprise an inductive charging module, and the digital electronics subsystem 110 can also comprise a coil of wire and associated electronics that function to allow inductive coupling of power between the external charging module 210 and the charger/battery. The charging coil preferably converts energy from an alternating electromagnetic field (e.g., provided by a charging dock or other adapter), into electrical energy to charge the battery and/or to power the system 100. Inductive charging allows electrical isolation between the external power supply of the external charging module 210 and internal electronics of the electronics subsystem 160 to facilitate increased user safety. Inductive charging provided by the charging coil thus also facilitates patient mobility while interacting with the system 100, such that the patient can be extremely mobile while managing his or her pain with the system 100. In alternative variations, however, the charging coil can be altogether omitted.

The system 100 and/or method of the preferred embodiment and variations thereof can be embodied and/or implemented at least in part as a machine configured to receive a computer-readable medium storing computer-readable instructions. The instructions are preferably executed by computer-executable components preferably integrated with the system 300 and one or more portions of the processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the field of biosignals will recognize from the previous detailed description and from the figures and claims, modifications and changes can be made to the preferred embodiments of the invention without departing from the scope of this invention defined in the following claims.

We claim:

1. A system for detecting bioelectrical signals of a user comprising:
    a set of sensors configured to detect EEG signals from the user, each sensor in the set of sensors comprising a semi-dry hydrogel with a non-volatile fluid configured to provide non-polarizable contact, the set of sensors including a first anterior frontal sensor, a second anterior frontal sensor, a first temporal lobe sensor, a second temporal lobe sensor, and a central sensor;
    an electronics subsystem comprising a power module configured to distribute power to the system and a signal processing module configured to process EEG signals from the set of sensors;
    a housing configured to be worn at a head region of the user, configured to couple to the electronics subsystem, and comprising a set of arms, wherein the set of arms includes a first arm originating proximal a first temporal bone of the user and that positions the first anterior frontal sensor proximal an anterior portion of the frontal bone of the user, a second arm originating proximal the first temporal bone of the user and that positions the second anterior frontal sensor proximal a lateral portion of the frontal bone of the user, and a third arm originating proximal the first temporal bone of the user and that positions the first temporal lobe sensor proximal the first temporal bone of the user, upon coupling of the system to the user; and a set of sensor interfaces coupling the set of sensors to the electronics subsystem through the set of arms of the housing, each sensor interface in the set of sensor interfaces comprising a pre-gain coupling and pre-gain level shift coupled to an amplifier, wherein the amplifier is coupled to a post-gain coupling and post-gain level shift coupled to the electronics system.

2. The system of claim 1, wherein the set of arms further comprises a fourth arm originating proximal the first temporal bone of the user and that positions the second temporal lobe sensor proximal the second temporal bone of the user, and a fifth arm, originating proximal the first temporal bone of the user and that positions the central sensor proximal a superior portion of the parietal bone of the user upon coupling of the system to the user.

3. The system of claim 1, wherein each sensor interface of the set of interfaces is mounted directly onto a corresponding sensor of the set of sensors, proximal to a set of sensor-user interfaces defined between the set of sensors and skin of the scalp of the user, upon coupling of the system to the user.

4. The system of claim 1, wherein each sensor of the set of sensor includes a sensor pad composed of a hypoallergenic polyhydroxyethylmethacrylate hydrogel saturated with non-volatile electrolyte configured to provide non-polarizable contact upon coupling of the system to the user.

5. The system of claim 4, wherein a distal portion of each arm of the set of arms includes an opening from which the sensor pad exudes, and a tapered end configured to facilitate hair displacement in coupling the set of sensors to skin of the user, upon coupling of the system to the user.

6. The system of claim 5, wherein the distal portion of each arm of the set of arms is configured to be reversibly coupled from the housing, and comprises the sensor pad positioned between a cap and an electrical contact, wherein the cap is sealed to a top layer surrounding the electrical contact.

7. The system of claim 1, wherein the electronics subsystem is configured to support input impedances from 1 MΩ to 1 GΩ, characteristic of an interface between the dry hydrogel and skin of the user upon coupling of the system to the user, by way of the set of sensor interfaces mounted directly to the set of sensors.

8. A system for detecting bioelectrical signals of a user comprising:
a set of sensors configured to detect bioelectrical signals from the user, each sensor in the set of sensors comprising a semi-dry hydrogel with a non-volatile fluid configured to provide non-polarizable contact;
an electronics subsystem comprising a power module configured to distribute power to the system and a signal processing module configured to process bioelectrical signals from the set of sensors;
a set of sensor interfaces configured to couple the set of sensors to the electronics subsystem and configured to block direct current signals in preprocessing signals transmitted to the electronics subsystem; and
a housing coupled to the electronics subsystem and comprising a set of arms, each arm in the set of arms housing a sensor of the set of sensors and configured to guide the sensor toward a terminal position at a head region of the user.

9. The system of claim 8, wherein each sensor interface in the set of sensor interfaces comprises a pre-gain AC coupling and pre-gain level shift coupled to an amplifier, wherein the amplifier is coupled to a post-gain coupling and post-gain level shift, configured to center an output of the post-gain coupling and post-gain level shift about a midrail voltage provided by the electronics subsystem.

10. The system of claim 9, wherein the set of sensors comprises a first anterior frontal sensor configured to detect EEG signals from a first frontal lobe region, a second anterior frontal sensor configured to detect EEG signals from a second frontal lobe region, a first temporal lobe sensor configured to detect EEG signals from a first temporal lobe region, a second temporal lobe sensor configured to detect EEG signals from a second temporal lobe region, and a central sensor configured to detect EEG signals from a parietal lobe region upon coupling of the system to the user.

11. The system of claim 10, wherein the set of arms includes: a first arm, originating proximal a first temporal bone of the user and terminating proximal the frontal bone of the user, that positions the first anterior frontal sensor proximal an anterior portion of the frontal bone of the user; and a second arm, originating proximal the first temporal bone of the user and terminating proximal the frontal bone of the user, that positions the second anterior frontal sensor proximal a lateral portion of the frontal bone of the user upon coupling of the system to the user.

12. The system of claim 11, wherein the set of arms includes: a third arm, originating proximal the first temporal bone of the user and terminating proximal an inferior portion of the first temporal bone of the user, that positions the first temporal lobe sensor proximal the first temporal bone of the user; and a fourth arm, originating proximal the first temporal bone of the user and terminating proximal a second temporal bone of the user, that positions the second temporal lobe sensor proximal the second temporal bone of the user.

13. The system of claim 12, wherein the set of arms includes a fifth arm, originating proximal the first temporal bone of the user and terminating proximal the parietal bone of the user, that positions the central sensor proximal a superior portion of the parietal bone of the user.

14. The system of claim 9 wherein each sensor interface of the set of interfaces is mounted directly onto a corresponding sensor of the set of sensors, proximal to a set of sensor-user interfaces defined between the set of sensors and skin of the scalp of the user, upon coupling of the system to the user.

15. The system of claim 14, wherein the set of interfaces is in communication with the electronics subsystem by way of the set of arms of the housing.

16. The system of claim 8, wherein each sensor of the set of sensors includes a sensor pad composed of a polyhydroxyethylmethacrylate hydrogel saturated with non-volatile electrolyte configured to provide non-polarizable contact upon coupling of the system to the user.

17. The system of claim 16, wherein a distal portion of each arm of the set of arms includes an opening from which the sensor pad exudes, and a tapered end configured to facilitate hair displacement in coupling the sensor pad to skin of the scalp of the user, upon coupling of the system to the user.

18. The system of claim 17, wherein the distal portion of each arm of the set of arms is configured to be reversibly coupled from the housing, and comprises the sensor pad positioned between a cap and an electrical contact, wherein the cap is sealed to a top layer surrounding the electrical contact.

19. The system of claim 8, wherein the electronics subsystem is configured to support input impedances from 1 $M\Omega$ to 1 $G\Omega$, characteristic of an interface between the dry hydrogel and skin of the user upon coupling of the system to the user, by way of the set of sensor interfaces coupled to the set of sensors.

20. The system of claim 8, wherein the set of arms extend from the housing from a position adjacent to a single temporal bone of the user, upon coupling of the system to the user, such that the housing is asymmetric about the head region of the user.

\* \* \* \* \*